US011248232B2

(12) United States Patent
Tanaka et al.

(10) Patent No.: US 11,248,232 B2
(45) Date of Patent: Feb. 15, 2022

(54) METHOD OF MODIFYING GENOME OF ORGANISM AND USE THEREOF

(71) Applicants: KABUSHIKI KAISHA TOYOTA CHUO KENKYUSHO, Nagakute (JP); The University of Tokyo, Tokyo (JP); MEIJI UNIVERSITY, Tokyo (JP)

(72) Inventors: Hidenori Tanaka, Nagakute (JP); Nobuhiko Muramoto, Nagakute (JP); Hiroki Sugimoto, Nagakute (JP); Norihiro Mitsukawa, Nagakute (JP); Chikara Ohto, Toyota (JP); Satoshi Kondo, Miyoshi (JP); Kunihiro Ohta, Tokyo (JP); Takahiro Nakamura, Tokyo (JP); Shuichi Osato, Kawasaki (JP)

(73) Assignees: KABUSHIKI KAISHA TOYOTA CHUO KENKYUSHO, Nagakute (JP); THE UNIVERSITY OF TOKYO, Tokyo (JP); MEIJI UNIVERSITY, Tokyo (JP)

( * ) Notice: Subject to any disclaimer, the term of this patent is extended or adjusted under 35 U.S.C. 154(b) by 99 days.

(21) Appl. No.: 16/060,897

(22) PCT Filed: Dec. 12, 2016

(86) PCT No.: PCT/JP2016/005110
§ 371 (c)(1),
(2) Date: Jun. 8, 2018

(87) PCT Pub. No.: WO2017/098734
PCT Pub. Date: Jun. 15, 2017

(65) Prior Publication Data
US 2018/0371477 A1 Dec. 27, 2018

(30) Foreign Application Priority Data
Dec. 11, 2015 (JP) .............................. JP2015-242684

(51) Int. Cl.
*C12N 15/82* (2006.01)
*C12N 15/10* (2006.01)
*C12N 15/01* (2006.01)

(52) U.S. Cl.
CPC ......... *C12N 15/8213* (2013.01); *C12N 15/01* (2013.01); *C12N 15/102* (2013.01)

(58) Field of Classification Search
None
See application file for complete search history.

(56) References Cited

U.S. PATENT DOCUMENTS

2008/0166809 A1* 7/2008 Ohta .................. C12N 9/16
435/441
2011/0277189 A1  11/2011 Kondo et al.
2012/0230971 A1* 9/2012 Choulika et al. ....... A61P 43/00
424/94.6
2013/0007911 A1* 1/2013 Stewart ............... C12N 15/827
800/278
2013/0217131 A1  8/2013 Kim et al.
2014/0273126 A1  9/2014 Muramoto et al.
2018/0184606 A1  7/2018 Muramoto et al.

FOREIGN PATENT DOCUMENTS

| JP | H11-151050 A | 6/1999 |
| JP | 2006-141322 A | 6/2006 |
| JP | 2011-160798 A | 8/2011 |
| JP | 2012-044883 A | 3/2012 |
| JP | 2014-171466 A | 9/2014 |
| JP | 2017-012145 A | 1/2017 |
| WO | WO 2015/026886 A1 * | 2/2015 |
| WO | 2017/002977 A1 | 1/2017 |

OTHER PUBLICATIONS

Takara's WWW site, Msel, accessed Feb. 3, 2020.*
Pray (2008) Nat Ed 1(1):204.*
Nesmelova & Hackett (2012) Adv Drug Deliv Rev 62(12):1187-95.*
Leonen et al. (2013) Nucl Acids Res 42(1):3-19.*
Plessis et al. (1992) Genetics 130(3):451-60.*
Faust & Heins (1998) J Amer Soc Hort Sci 123(2):208-14.*
Faust & Heins (1998) J Am Horticult Soc 123:208.*
Endo et al., "A Novel Pollen-Pistil Interaction Conferring High-Temperature Tolerance during Reproduction via CLE45 Signaling," Current Biology, Sep. 9, 2013, vol. 23, p. 1670-1676.
Schlenker et al., "Nonlinear temperature effects indicate severe damages to U.S. crop yields under climate change," PNAS, Sep. 15, 2009, vol. 106, No. 37, pp. 15594-15598.
Mar. 14, 2017 International Search Report issued in International Patent Application No. PCT/JP2016/005110.
Mar. 14, 2017 Written Opinion of the International Searching Authority issued in International Patent Application No. PCT/JP2016/005110.
Johansen, Elisabeth, "Intron insertion facilitates amplification of cloned virus cDNA in *Escherichia coli* while biological activity is reestablished after transcription in vivo," Proc. Natl. Acad. Sci, USA, Oct. 1996, vol. 93, pp. 12400-12405.
Mar. 13, 2018 Office Action issued in Japanese Patent Application No. 2015-242684.
Oct. 2, 2018 Japanese Office Action issued in Patent Application No. 2015-242684.
Ashraf, M. et al. "Alteration of Gene Expression by Restriction Enzymes Electroporated into Plant Cells" Mutation Research, 1993, vol. 302, pp. 75-82.

(Continued)

*Primary Examiner* — Russell T Boggs
(74) *Attorney, Agent, or Firm* — Oliff PLC

(57) ABSTRACT

A method of modifying the genome of an organism, wherein the modification method includes modifying the genome of the organism by using in a cell of the organism a protein having an optimal temperature for double-stranded DNA breakage activity in an ordinary temperature region.

20 Claims, 9 Drawing Sheets

Specification includes a Sequence Listing.

(56) References Cited

OTHER PUBLICATIONS

Winegar, R. A. et al. "Cell Electroporation is a Highly Efficient Method for Introducing Restriction Endonucleases into Cells" Mutation Research, 1989, vol. 225, pp. 49-53.
Lewis, L. K. et al. "Requirement for end-joining and checkpoint functions, but not RAD52-mediated recombination, after EcoRI endonuclease cleavage of *Saccharomyces cerevisiae* DNA" Molecular and Cellular Biology, 1998, vol. 18, No. 4, pp. 1891-1902.
Sep. 15, 2020 Office Action issued in Japanese Patent Application No. 2018-17310.
Cosmo Bio Co., Ltd., FastDigest Restriction Enzyme, Published Jun. 1, 2010. <https://www.cosmobio.co.jp/upfiles/catalog/pdf/catalog_11363.pdf>.

\* cited by examiner

FIG.1
(A) *FLAG-iHinP1I-NLS*
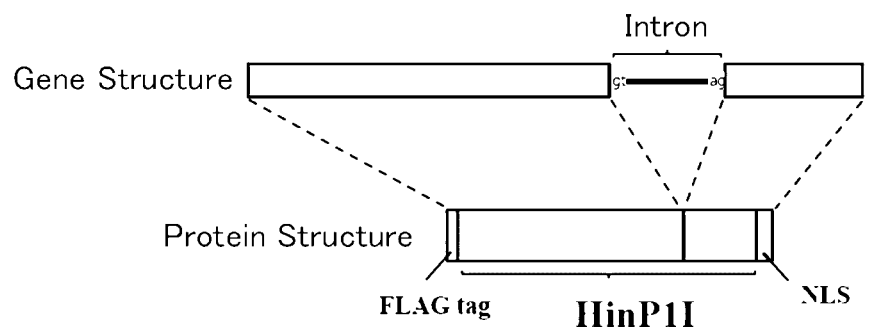
(B) *FLAG-iMseI-NLS*
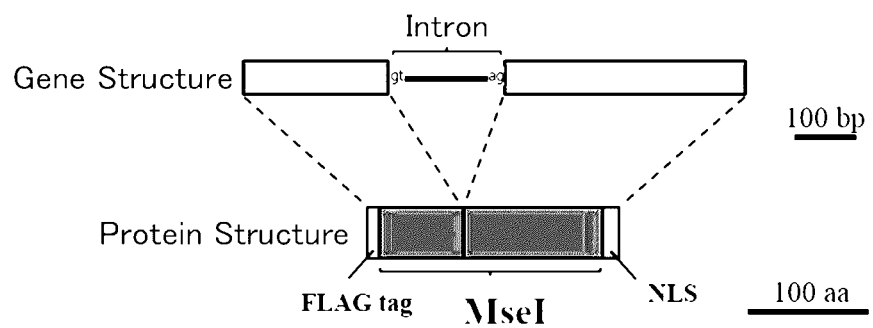

[Fig. 13]

```
                        SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
cggctaccac atccaaggaa                                                  20

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
tgtcactacc tccccgtgtc a                                                21

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
ccatgtattt tgcaatgcgt g                                                21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
tgtggagcac ctcgaatctc t                                                21

<210> SEQ ID NO 5
<211> LENGTH: 48
<212> TYPE: DNA
<213> ORGANISM: Artificial Sequence
<220> FEATURE:
<223> OTHER INFORMATION: Primer

<400> SEQUENCE: 5
cataaaatat tcagcgaatt ggatccatgg attacaagga cgatgatg                   48

<210> SEQ ID NO 6
<211> LENGTH: 49
<212> TYPE: DNA
<213> ORGANISM: Artificial Sequence
<220> FEATURE:
<223> OTHER INFORMATION: Primer

<400> SEQUENCE: 6
gatggtgatg cgatcctctc tgcagtcaac ctccaacctt cctcttctt                  49
```

<210> SEQ ID NO 7
<211> LENGTH: 49
<212> TYPE: DNA
<213> ORGANISM: Artificial Sequence
<220> FEATURE:
<223> OTHER INFORMATION: Primer

<400> SEQUENCE: 7
cataaaatat tcagcgaatt ggatccatgg attacaagga cgatgatga        49

<210> SEQ ID NO 8
<211> LENGTH: 49
<212> TYPE: DNA
<213> ORGANISM: Artificial Sequence
<220> FEATURE:
<223> OTHER INFORMATION: Primer

<400> SEQUENCE: 8
gatggtgatg cgatcctctc tgcagtcaac ctccaacctt cctcttctt        49

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
agatctatgg attacaagga cgatga        26

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
gagctctcaa cctccaacct tcctct        26

<210> SEQ ID NO 11
<211> LENGTH: 72
<212> TYPE: DNA
<213> ORGANISM: Artificial Sequence
<220> FEATURE:
<223> OTHER INFORMATION: Primer

<400> SEQUENCE: 11
gtaaaatcgg ttaatttccc ctttctttct tttcctcact ccgaagtgta catacctttt        60
cactctgagt cc        72

<210> SEQ ID NO 12
<211> LENGTH: 75
<212> TYPE: DNA
<213> ORGANISM: Artificial Sequence
<220> FEATURE:
<223> OTHER INFORMATION: Primer

<400> SEQUENCE: 12
gaaaagaaag aaagggggaaa ttaaccgatt ttactaacac tgacactttg aacaggtctg        60
gatcttctga tgctg        75

<210> SEQ ID NO 13
<211> LENGTH: 75

```
<212> TYPE: DNA
<213> ORGANISM: Artificial Sequence
<220> FEATURE:
<223> OTHER INFORMATION: Primer

<400> SEQUENCE: 13
aggtctcaaa aacgtaaata aacttaaaag ataattaacc actgaatgaa catacctttt    60
cactctgagt ccctt                                                    75

<210> SEQ ID NO 14
<211> LENGTH: 75
<212> TYPE: DNA
<213> ORGANISM: Artificial Sequence
<220> FEATURE:
<223> OTHER INFORMATION: Primer

<400> SEQUENCE: 14
taattatctt ttaagtttat ttacgttttt gagaccttac taacgaccag gataggtctg    60
gatcttctga tgctg                                                    75
```

METHOD OF MODIFYING GENOME OF ORGANISM AND USE THEREOF

TECHNICAL FIELD

The present disclosure relates to a method of modifying a genome of an organism and use of the method.

BACKGROUND ART

Increasing the mass (biomass) of biological resources, in particular increasing plant biomass is effective not only for increasing food production, but also for global environmental conservation, preventing global warming, and reducing greenhouse gas emissions. The creation of technology for increasing plant biomass and creation of useful plants are therefore extremely important.

In addition, microorganisms are being effectively utilized in various industries. For example, in bioethanol production starting from a polysaccharide such as cellulose, yeasts having properties such as resistance to high temperatures, resistance to high alcohol concentrations, and a high alcohol synthesis capacity hold out promise for carrying out ethanol fermentation at lower costs.

Many of characteristics exhibited by various eukaryotes, including useful plant bodies and microorganisms, are quantitative traits that are generally influenced by the expression of a number of genes rather than by a single gene by itself. When modification of the quantitative trait is pursued by ordinary mutagenesis, treatment over a large number of generations ends up being required due to a small trait change provided by each single operation.

The developments have thus been reported of methods that can efficiently carry out large-scale genomic rearrangement in order to modify quantitative traits (Patent Literature 1, Patent Literature 2, and Patent Literature 3). It is reported that, using these methods, whole genome DNA breakage can be induced by causing a transient expression in a cell of a so-called restriction enzyme, thus simultaneously realizing a large number of multiple genomic rearrangements and efficiently obtaining a mutant population having diverse genomic constitutions. In these methods, for example, a gene encoding a double-stranded DNA breakage enzyme such as a heat-resistant high-frequency restriction enzyme, e.g., the TaqI gene, is introduced into a plant cell, and operation on the genome is then brought about by the transient activation of the restriction enzyme at a temperature that can avoid damage to the cell but which is at least as high as a temperature at which the restriction enzyme is activated, for example, 37 deg C.

On the other hand, for example, in plants, it is known that, for example, the reproductive growth phase of flowering plants is extremely vulnerable to high temperatures (Non Patent Literature 1). High temperatures have also been reported to be a strong stressor that substantially affects the growth and yield of crops (Non Patent Literature 2).

CITATION LIST

Patent Literature

[Patent Literature 1] Japanese Patent Application Publication No. 2011-160798
[Patent Literature 2] Japanese Patent Application Publication No. 2006-141322
[Patent Literature 3] Japanese Patent Application Publication No. 2012-44883
[Patent Literature 4] Japanese Patent Application Publication No. H11(1999)-151050

Non Patent Literature

[Non Patent Literature 1] Endo, S., Shinohara, H., Matsubayashi, Y., & Fukuda, H., Current Biology, 2013; 23(17): 1670-1676
[Non Patent Literature 2] Schlenker, W., & Roberts, M. J., PNAS. 2009; 106(37): 15594-15598

SUMMARY OF INVENTION

According to the present inventors, thermophile-derived restriction enzymes have been used in order to avoid the operation of these enzymes at the growth temperature of the organism. However, it was found that a load on the plant or microorganism was larger than predicted even in a case of a temporary activation treatment (heat treatment) of the double-stranded DNA breakage enzyme at temperatures of about 37 deg C., which are substantially lower than the optimal temperature of such thermophile-derived restriction enzymes. Due to this, raising the treatment temperature and increasing a treatment time were highly problematic approaches to increasing a degree and a variety of genomic modification.

In addition, depending in particular on plant species, organs, and growth stages, the effect of the thermal load was even larger and the DNA breakage efficiency was also low and genetic recombination could also not be realized.

As such, it has been found that genomic modification based on a heat treatment-induced activation of the double-stranded DNA breakage enzyme using such a thermophile-derived restriction enzyme could cause the resulting thermal load on the microorganism or plant body and an extent of the modification to be problematic.

The present disclosure thus provides an art that realizes an effective genomic modification while reducing a load on an organism that is a target of modification.

In order to lower the thermal load, the present inventors focused on an optimal temperature for the double-stranded DNA breakage enzyme. It was thought up to now that the action of a protein that had an optimal temperature for its double-stranded DNA breakage activity in the neighborhood of an organism's growth temperature yielded excessively large adverse effects on the survival and growth of the organism. However, knowledge has been obtained to the effect that a more effective genomic modification could be effectively realized when the thermal load on the organism was prevented or inhibited by deliberately using a double-stranded DNA breakage enzyme having an optimal temperature in the vicinity of the organism's growth temperature and as necessary by controlling the functional state of the double-stranded DNA breakage enzyme. The present disclosure provides the following means based on this knowledge.

The present disclosure provides a method of modifying a genome of an organism, wherein the modification method comprises modifying a genome of an organism using, in a cell of the organism, a protein having an optimal temperature for double-stranded DNA breakage activity in an ordinary temperature region.

The present disclosure provides a method of producing a population of genomically modified organisms, wherein the production method comprises modifying the genome of a parent organism by bringing about the action, in a cell of the parent organism, of a protein having an optimal temperature for double-stranded DNA breakage activity in an ordinary temperature region.

The present disclosure provides a method of producing a genomically modified organism, wherein the production method comprises:

modifying the genome of a parent organism by bringing about the action, in a cell of the parent organism, of a protein having an optimal temperature for double-stranded DNA breakage activity in an ordinary temperature region; and selecting, based on an indicator, an intended eukaryotic organism from a population of eukaryotic organisms that carry modified genomes.

The present disclosure provides a breeding material comprising DNA that has a coding region that encodes a protein that has a double-stranded DNA breakage activity that exhibits an optimal temperature in an ordinary temperature region. The coding region contains an intron that is not processed within the host for the breeding material.

BRIEF DESCRIPTION OF DRAWINGS

FIG. 1 is a diagram that shows gene and protein structures for intron-incorporating ordinary-temperature restriction enzymes.

DESCRIPTION OF EMBODIMENTS

Figure 2:
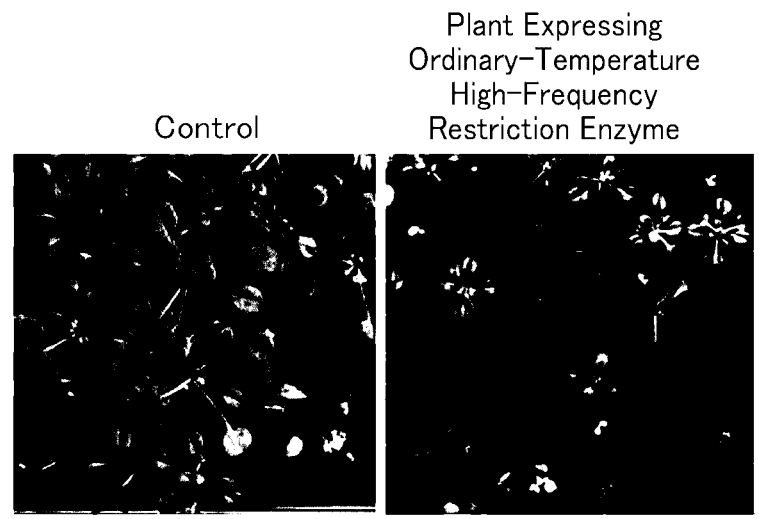
FIG. 2 is a photo that shows a delay in growth of a plant that expresses the ordinary-temperature restriction enzyme under normal growth conditions.

The present disclosure relates to a method of modifying a genome of an organism and to use of the modification method. When modifying the genome of the organism, the present modification method can comprises modifying the genome of the organism by the action, in a cell of the organism, of a protein having an optimal temperature for double-stranded DNA breakage activity in an ordinary temperature region. According to the present modification method, genomic modification can be effectively achieved by having genomic rearrangement co-exist in good balance with a reduction in a load on the organism. As a result, genetic rearrangement of the genome of the organism can be promoted and rearrangement of the genome can thus be brought about.

The protein having the double-stranded DNA breakage activity used in the present modification method has its optimal temperature in an ordinary temperature region. Due to this, the temperature for inducing the appearance of the double-stranded DNA breakage activity can be restrained and a time can be shortened. This serves to restrain a thermal load on the organism.

On the other hand, the present inventors expected that, due to the action of such a protein having its optimal temperature in the ordinary temperature region that is near to the suitable growth temperature of the organism, there would be an increase in the adverse effects on the growth activity of the organism and thus on its survival. However, contrary to the expectations of the inventors, it has been found that, notwithstanding the effects, for instance, on the organism growth under conditions where this protein is intended to function, adverse effects due to the function of this protein are suppressed or avoided under conditions where the function of this protein is not intended or under conditions where the function is inhibited. As a result, it has been found that genomic modification can be achieved by effectively inducing, in the genome of the organism, genomic rearrangements such as translocations, inversions, duplication, and so forth, and various mutations such as point mutations, chromosomal aneuploidy, and so forth. As a consequence, a population of organisms having diverse altered traits can be rapidly obtained by using the present modification method.

In addition, the present modification method can, while restraining the thermal load, bring about a satisfactory action by the aforementioned protein even in, for example, various growth stages, organs, or tissues of an organism, which has heretofore been quite difficult. As a result, it becomes possible to modify the genome of an organism in a time period and/or at a location where an effective genomic modification holds out promise from a standpoint of a diversity of the obtained organisms and a modification efficiency.

According to the present inventors, the induction of genomic rearrangement by genetic recombination using the transient thermal activation of a heat-resistant restriction enzyme has not necessarily been satisfactory in the past. It has been weak in particular with regard to various growth stages, e.g., seed, shoot apex, lateral buds, and flower buds, and in tissues and organs. However, the present modification method enables creation through the induction of genomic modification of a sufficient diversity in the genome and cells for various growth stages, e.g., seed, shoot apex, lateral buds, and flower buds, and in tissues and organs.

For example, with seeds, since the individual size is small, a library that will enable the induction of genomic modification by using a large plant body mass can be produced at an accelerated rate. In addition, for example, the induction of genomic rearrangement at the shoot apex is effective for the breeding of vegetatively propagating plants, while flower buds are a tissue where cells destined to be transmitted to the next generation are reliably present and are effective for an efficient induction of genomic rearrangement.

The herein disclosed method of producing an organism population by using the present modification method, because it comprises a modification step in which the aforementioned protein is caused to act on a parent organism, can efficiently produce an organism population that is more highly diverse than heretofore. Moreover, a target organism can be obtained from a highly diverse population of organisms using the herein disclosed method of producing an organism using the present modification method.

Based on the preceding, the present disclosure also provides the following modification method.

(1) A method of modifying the genome of an organism, wherein the modification method comprises modifying the genome of the organism by using in a cell of the organism a protein having an optimal temperature for double-stranded DNA breakage activity in an ordinary temperature region.

(2) The modification method according to (1), wherein the protein is a restriction enzyme originating from a bacterium that is not a thermophile.

(3) The modification method according to (1) or (2), wherein the optimal temperature for the double-stranded DNA breakage activity of the protein is at least 25 deg C. and not more than 40 deg C.

(4) The modification method according to any of (1) to (3), wherein the organism is a eukaryotic organism.

(5) The modification method according to any of (1) to (4) wherein the modifying is carried out at at least 20 deg C. and not more than 45 deg C.

(6) The modification method according to (5), wherein the modifying is carried out for at least 10 minutes and not more than 3 hours.

(7) The modification method according to any of (1) to (6) that uses the protein as obtained by the expression of an exogenous gene that encodes the protein.

(8) The modification method according to any of (1) to (7), wherein the modifying comprises controlling the production of the protein to a degree that enables modification of the genome while maintaining the growth capacity of the organism.

(9) The modification method according to (7) or (8), wherein the modifying comprises modifying the genome of the organism by inducing the expression of the exogenous gene.

(10) The modification method according to any of (7) to (9), wherein the modifying comprises modifying the genome of the organism by the continuous maintenance of the expression of the exogenous gene.

(11) The modification method according to any of (1) to (6), wherein the modifying comprises causing the action of the protein by directly supplying it into a cell of the organism.

(12) The modification method according to any of (1) to (10), wherein the protein is one or two or more restriction enzymes selected from the group consisting of HinP1I, MseI, HaeIII, AluI, MboI, and HbaI.

(13) The modification method according to any of (1) to (12), wherein the organism is a plant body or a portion of a plant.

(14) The modification method according to (13), in which the plant body or the portion of the plant is one or more selected from the group consisting of a seed, a shoot apex, a lateral bud, a flower bud, pollen, an ovary, an endosperm, an embryo, and a portion of a seed, a shoot apex, a lateral bud, a flower bud, pollen, an ovary, an endosperm, an embryo.

(15) The modification method according to any of (1) to (12), in which the organism is a microorganism.

(16) A method of producing a population of genomically modified organisms, wherein the production method comprises modifying the genome of a parent organism by causing the action within a cell of the parent organism of a protein having an optimal temperature for double-stranded DNA breakage activity in an ordinary temperature region.

(17) A method of producing a genomically modified organism, wherein the production method comprises:
modifying the genome of a parent organism by causing the action in a cell of the parent organism of a protein having an optimal temperature for double-stranded DNA breakage activity in an ordinary temperature region; and
selecting an intended eukaryotic organism from a population of eukaryotic organisms that carry modified genomes based on an indicator.

(18) A breeding material wherein the breeding material comprises DNA that has a coding region that encodes a protein that has a double-stranded DNA breakage activity that exhibits an optimal temperature in an ordinary temperature region wherein the coding region contains an intron that is not processed within a host for the breeding material.

(19) The breeding material according to (18), which is an expression vector for a eukaryotic organism.

(20) The breeding material according to (18) or (19), wherein the host is a prokaryotic organism.

In the present disclosure, "genome" refers to DNA that exists in an organism as chromosomal DNA, is capable of self-replication in cells of the organism, and is transmitted to daughter cells. For eukaryotic cells, this can encompass mitochondrial DNA in addition to the chromosomal DNA present in the nucleus.

Also in the present disclosure, "genetic recombination" means in a broad sense DNA cleavage and rebonding phenomena that are produced in a cell. In the present invention, "genetic recombination" encompasses homologous recombination, nonhomologous recombination, gene conversion, inversion, unequal crossover, crossover, translocation, copy number variation, chromosome fusion, and mutation.

In the present disclosure, "ordinary temperature region" means at least 15 deg C. and not more than 42 deg C., more preferably at least 15 deg C. and not more than 40 deg C., even more preferably at least 25 deg C. and not more than 40 deg C., even more preferably at least 25 deg C. and not more than 37 deg C., and still more preferably at least 30 deg C. and not more than 37 deg C.

Typical and non-limiting specific examples of the disclosures of the Description are explained in detail below with reference to the drawings. These detailed explanations are aimed simply at showing preferred examples of the disclosures in detail so that they can be implemented by a person skilled in the art, and are not intended to limit the scope of the disclosures of the Description. The additional features and disclosures disclosed below may be used separately or together with other features and inventions to provide a further improved method of detecting a target nucleic acid or the like.

The combinations of features and steps disclosed in the detailed explanations below are not essential for implementing the disclosures in the broadest sense, and are presented only for purposes of explaining typical examples of the disclosures in particular. Moreover, the various features of the typical examples above and below and the various features described in the independent and dependent claims do not have to be combined in the same way as in the specific examples described here, or in the listed order, when providing addition useful embodiments of the disclosures.

All features described in the disclosure are intended as individual and independent disclosures restricting the initial disclosures and the claimed matter specifying the invention, separately from the constitution of features described in the Examples and/or Claims. Moreover, all descriptions of numerical ranges and groups or sets are intended to include intermediate configurations for purposes of restricting the initial disclosures and the claimed matter specifying the invention.

Embodiments of the present disclosure are described in detail in the following.

(Method of Modifying a Genome of an Organism)

The herein disclosed method of modifying a genome of an organism (referred to below as a present modification method) can comprise a modification step of modifying the genome of the organism by bringing about action in a cell of the organism in the ordinary temperature region of a protein that has a double-stranded DNA breakage activity (referred to hereinbelow as the present protein).

(Modification Step)

(Organism)

The present modification method can be applied to any organism. The organism includes eukaryotic organisms and prokaryotic organisms. The eukaryotic organism can be an animal body, plant body, or eukaryotic microorganism. The animals are not particularly limited and can be exemplified by mammals, non-mammalian animals such as various fish, and portions of these. The animal bodies or portions thereof, are sufficient as far as they are originated from an animal and may take the form of any of, e.g., cells, tissues, organs, unfertilized eggs, fertilized eggs, and so forth. It is convenient for obtaining a modified animal when this retains a capacity to regenerate a complete animal, as with, e.g., a fertilized egg.

There are no particular limitations on the plant body, and it may be, for example, a portion of a dicot or, for example, a portion of a monocot (see below) belonging to, e.g., Brassicaceae, Graminiae, Solanaceae, Leguminosae, or Salicaceae.

Brassicaceae: Thale-cress (*Arabidopsis thaliana*), Oil seed rape (*Brassica rapa, Brassica napus*), Cabbage (*Brassica oleracea* var. *capitata*), Chinese cabbage (*Brassica rapa* var. *pekinensis*), Quib-geng-cai (*Brassica rapa* var. *chinensis*), Turnip (*Brassica rapa* var. *rapa*), Nozawana (*Brassica rapa* var. *hakabura*), Mizuna (*Brassica rapa* var. *lancinifolia*), Komatsuna (*Brassica rapa* var. *peruviridis*), Pak choi (*Brassica rapa* var. *chinensis*), Japanese radish (*Brassica Raphanus sativus*), Wasabi (*Wasabia japonica*) etc. Solanaceae: Tabaco (*Nicotiana tabacum*), Eggplant (*Solanum melongena*), Potato (*Solaneum tuberosum*), Tomato (*Lycopersicon lycopersicum*), Japanese pepper (*Capsicum annuum*), Petunia (*Petunia*) etc. Leguminosae: Soybean (*Glycine max*), Garden pea (*Pisum sativum*), broad bean (*Vicia faba*), Wisteria (*Wisteria floribunda*), Peanut (*rachis.*

*Hypogaea*), Lotus (*Lotus corniculatus* var. *japonicus*), Common bean (*Phaseolus vulgaris*), Adzuki bean (*Vigna angularis*), Acacia (*Acacia*) etc. Asteraceae: Chrysanthemum (*Chrysanthemum morifolium*), Sunflower (*Helianthus annuus*) etc. Arecaceae: Oil palm (*Elaeis guineensis, Elaeis oleifera*), Coconut palm (*Cocos nucifera*), Date palm (*Phoenix dactylifera*), carnauba (*Copernicia*) etc. Anacardiaceae: Wax tree (*Rhus succedanea*), Cashewnut tree (*Anacardium occidentale*), Japanese lacquer (*Toxicodendron vernicifluum*), Mango (*Mangifera indica*), Pistacio (*Pistacia vera*) etc. Cucurbitaceae: Squash (*Cucurbita maxima, Cucurbita moschata, Cucurbita pepo*), Cucumber (*Cucumis sativus*), Snake goud (*Trichosanthes cucumeroides*), Bottole gourd (*Lagenaria siceraria* var. *gourda*) etc. Rosaceae: Almond (*Amygdalus communis*), Rose (*Rosa*), Strawberry (*Fragaria*), Cherry blossom (*Prunus*), Apple (*Malus pumila* var. *domestics*) etc. Caryophyllaceae: Carnation (*Dianthus caryophyllus*) etc. Salicaceae: Poplar (*Populus trichocarpa, Populus nigra, Populus tremula*) etc. Gamineae: field corn (*Zea mays*), Rice (*Oryza sativa*), barley (*Hordeum vulgare*), bread wheat (*Triticum aestivum*), Bamboo (*Phyllostachys*), Sugar cane (*Saccharum officinarum*), Napier grass (*Pennisetum pupureum*), Erianthus (*Erianthus ravenae*), Miscanthus (Japanese silver grass) (*Miscanthus virgatum*), Kaffir corn (orghum), Switch grass (*Panicum*) etc. Liliaceae: Tulip (*Tulipa*), lily (*Lilium*) etc. Mytrease: Eucalyptus (*Eucalyptus camaldulensis, Eucalyptus grandis*) etc.

The plant body used in the present modification method may be sufficient as far as it is derived from a plant, and the plant body may take any form, e.g., cell, tissue, organ, seed, or callus. It is convenient for obtaining a modified plant when the capacity to regenerate the complete plant is appropriately retained.

There are also no particular limitations on the microorganism, and it can be exemplified by industrially useful eukaryotic microorganisms such as koji mold belonging to, e.g., genus *Aspergillus*, and various yeast belonging to genus *Saccharomyces*, e.g., *Saccharomyces cerevisiae*. The microorganism can also be exemplified by various Gram-positive bacteria, e.g., *Escherichia coli*, various lactic acid bacteria, e.g., genus *Lactobacillus*, and various Gram-positive bacteria, e.g., genus *Bacillus* such as *Bacillus subtilis*.

(Preparation of the Organism)

The present modification method uses various organisms or portions thereof, but the ploidy of the genomic set of the organism is not a particular consideration. That is, it may be a euploid that has the naturally occurring ploidy (euploidy) of the organism; or it may be a polyploid that has a ploidy exceeding the naturally occurring ploidy of the organism; or a polyploid that has the ploidy below the naturally occurring ploidy of the organism. In addition, it may be an autoploid or an allopolyploid. In addition to integral multiple polyploids, it may be an aneuploid exhibiting aneuploidy, in which the number of some of chromosome subsets is changed. The ploidy of the chromosomes of a eukaryote can be determined by heretofore known methods. In addition; it can be determined by a method such as flow cytometry or a tiling array.

(The Present Protein: Protein Having a Double-Stranded DNA Breakage Activity)

In the present step, the present protein, i.e., a protein having a double-stranded DNA breakage activity, is caused to act within a cell of an organism. There are no particular limitations on the present protein, and known double-stranded DNA breakage enzymes and their mutations can typically be used.

The double-stranded DNA breakage enzyme is preferably a double-stranded DNA breakage enzyme (restriction enzyme) for which the recognition site on the DNA is about 4 to 6 bases. Since the number of breakage sites in the genomic contributes to the efficiency of genetic recombination, the chromosomal DNA can be cut at a preferred frequency by having the recognition site be this number of bases. For example, a double-stranded DNA breakage enzyme for which the recognition site is 4 to 5 bases is more preferred, while a recognition site of 4 bases is even more preferred. There are no particular limitations on such double-stranded DNA breakage enzymes and various known restriction enzyme are examples. Double-stranded DNA breakage enzymes that have such recognition sites are generally also known as high-frequency restriction enzymes.

Restriction enzymes that have their optimal temperature (also known as a incubation temperature), i.e., the temperature giving roughly the maximum double-stranded DNA breakage enzymatic activity, not in a high temperature region but rather in a lower temperature region (such restriction enzymes are referred to as ordinary-temperature restriction enzymes in the following) can be used as the restriction enzyme. The high temperature region here can refer to the temperature region of at least 50 deg C. It is more preferably the temperature region of at least 45 deg C. Thus, the ordinary-temperature restriction enzyme in the present disclosure can be exemplified by enzymes that have their optimal temperature for double-stranded DNA breakage activity at less than 50 deg C., while restriction enzymes that have this optimal temperature at less than 45 deg C. are preferred.

The ordinary-temperature restriction enzyme can more preferably have its optimal temperature for double-stranded DNA breakage activity in the ordinary temperature region. Here, "ordinary temperature region" means at least 15 deg C. and not more than 42 deg C., more preferably at least 15 deg C. and not more than 40 deg C., even more preferably at least 25 deg C. and not more than 40 deg C., even more preferably at least 25 deg C. and not more than 37 deg C., and still more preferably at least 30 deg C. and not more than 37 deg C.

An ordinary-temperature restriction enzyme generally has its optimal temperature at about at least 25 deg C. and not more than 40 deg C. (typically 25 deg C. or 37 deg C.). In addition, the ordinary-temperature restriction enzyme can generally be inactivated by incubation for 15 to 20 minutes at 60 to 70 deg C. The temperature at which the enzymatic activity is deactivated by incubation for 15 to 20 minutes is designated as the inactivation temperature. Even the ordinary-temperature restriction enzyme may have the inactivation temperature of at least 80 deg C.

The DNA in a cell can be efficiently cut while avoiding adverse effects on the organism by using an ordinary-temperature restriction enzyme and as necessary by adjusting the amount of the restriction enzyme (amount of expression), its timing, temperature, and time of action, and other conditions for its action.

Restriction enzymes derived from bacteria that are not thermophiles (non-thermophile-derived restriction enzymes) can also be used as the restriction enzyme. Thermophiles are bacteria for which the optimal growth temperature is at least 45 deg C. or for which the growth temperature limit is at least 55 deg C. Thermophiles are generally archaea. Non-thermophile-derived restriction enzymes can generally be ordinary-temperature restriction enzymes. On the other hand, thermophile-derived restriction enzymes generally can have inactivation temperatures of 80 deg C. or more. In addition, the optimal temperatures for thermophile-derived restriction enzymes are about at least 37 deg C. and not more than 80 deg C.

Ordinary-temperature restriction enzymes and non-thermophile-derived restriction enzymes have a certain level of double-stranded DNA breakage activity in the temperature region of the temperatures commonly used for organisms (growth temperature or culture temperature), and as a consequence their strength (level) of action can be established with a high degree of freedom by adjusting the various conditions of action.

A commercially available restriction enzyme having an optimal temperature of about at least 25 deg C. and not more than 40 deg C. (typically 25 deg C. or 37 deg C.) can be used as the ordinary-temperature restriction enzyme. A commercially available restriction enzyme provided with such an optimal temperature and also having an inactivation temperature of at least 60 deg C. and not more than 70 deg C. can preferably be used.

In addition, a suitable selection from known non-thermophile-derived restriction enzymes can be used as the non-thermophile-derived restriction enzyme.

There are no particular limitations on such restriction enzymes, and they can be exemplified by AluI, HhaI, HinP1I, MseI, MboI, and HaeIII. The optimal temperature for all of these is 37 deg C. Additional examples are BfaI, BfuCII, Bsh1236I, BsuRI, DPnI, DpnII, FspBI, HaeIII, Hin1II, Hin6I, HpaII, HpyCH4V, MspI, NlaIII, RsaI, and Sau3AI. All of the restriction enzymes listed here have an optimal temperature of about 37 deg C. Additional examples are ApaI, BaeI, BspCNI, CviAII, CviQI, SmaI, and SwaI. These restriction enzymes engage in 4-base recognition and all have optimal temperatures of about 25 deg C.

Enzymes other than the above, i.e., thermophile-derived restriction enzymes and enzymes having an optimal temperature of at least 50 deg C., can also be used as the restriction enzyme. By suitably establishing the conditions for their action to adjust their strength of action, the DNA within a cell can be efficiently cut, while avoiding adverse effects on the organism, even through the action of such restriction enzymes at temperatures around the ordinary temperature region. Suitable known restriction enzymes can be used as such restriction enzymes.

The optimum temperature of the protein having a double-stranded DNA breakage activity, e.g., a restriction enzyme, is described in the protocol from the supplier for the enzyme or can be based on the results of an evaluation of the enzymatic reaction at various temperatures in the presence of a prescribed concentration of a prescribed substrate in a suitable buffer for the enzyme.

The method for measuring the optimal temperature of the restriction enzyme can be exemplified by a method in the literature (Greene, P. J., Poonian, M. S., Nussbaum, A. L., Tobias, L., Garfin, D. E., Boyer, H. W., & Goodman, H. M. (1975), Restriction and modification of a self-complementary octanucleotide containing the Eco RI substrate. Journal of Molecular Biology, 99(2), 237-261). Specifically, a quantitative analysis is performed on the cutting of SV40 DNA ($^{32}$P-labeled) by the restriction enzyme. That is, 5 uL (microliters) of a restriction enzyme solution (0.05 M potassium phosphate buffer (pH 7.0), 0.02 M NaCl, 0.02% NP40, 0.1 mM EDTA, 0.7 mM Beta-mercaptoethanol, and 0.7 pM restriction enzyme) is added to a total of 50 uL of a reaction solution (0.1 M Tris HCl (pH 7.5), 5 mM MgCl$_2$, 0.05 M NaCl, 1.6 pM, SV40 DNA), and treatment with the restriction enzyme is performed for a suitable time of around several minutes at respective temperatures (temperatures set at appropriate temperature intervals from about 0 to 80 deg C.). After the reaction is stopped by the addition of 1% SDS, the supercoil DNA (form I), open circle DNA (form II), and linear DNA (form III) are separated by agarose electrophoresis. The amount of radiation (cpm) for each form is measured and a number (pmol) of phosphodiester bonds cleaved open by treatment with the restriction enzyme is determined using the following formula. The number of phosphodiester bonds cleaved open at each temperature is graphed, and the vicinity of the peak value can be taken to be the optimal temperature (for the double-stranded DNA breakage activity) of each enzyme.

A number of phosphodiester bonds (pmol)=[2× amount of radiation (cpm) from form III+ amount of radiation (cpm) from form II)/(total amount of radiation (cpm) from forms I, II, and III)]×amount of DNA (pmol)

The inactivation temperature of the protein having a double-stranded DNA breakage activity, e.g., a restriction enzyme, can be obtained, for example, by measuring the activity before and after a heat treatment in which the enzyme is held for about 15 to 20 minutes at various temperatures. The temperature at which activity can no longer be detected is the inactivation temperature.

In order to cause the action of the present protein in a cell of the organism, at least the presence of the present protein in the cell is brought about. The present protein is natively present in the cell, but is preferably supplied from outside. The present protein may be directly supplied to the cells of the organism or may be supplied through the expression of an exogenous gene that codes for the present protein.

A vector that expresses the present protein in the cells of the organism can be constructed by the individual skilled in the art in accordance with heretofore known procedures in conformity as appropriate with the type of cell and the transformation procedure. The base sequence encoding the present protein can be acquired from various databases. In addition, a vector adapted to the cell can be acquired as appropriate, and in addition a desired expression cassette can be fabricated for which, for example, a suitable promoter, terminator, enhancer, and so forth have also been selected as appropriate. While there are no particular limitations here, a nuclear localization signal useful for the eukaryotic organism used is preferably provided.

For example, various heretofore known vectors can be used as the parent vector for the expression vector for bringing about protein expression in plant cells. For example, a plasmid, phage, or cosmid can be used and can be selected as appropriate in correspondence to the target plant cell and the method of introduction. Specific examples are vectors such as pBR322, pBR325, pUC19, pUC119, pBluescript, pBluescriptSK, and the pBI series. In particular, when the method for vector introduction into a plant body is a method that uses *Agrobacterium*, the use of the binary vectors of the pBI system is preferred. The binary vectors of the pBI series can be specifically exemplified by pBIG, pBIN19, pBI101, pBI121, pBI221, and the like.

There are no particular limitations on the promoter as long as the promoter can cause the expression of the restriction enzyme gene within the plant body, and known promoters can be used as appropriate. The promoter here can be exemplified by the cauliflower mosaic virus 35S promoter (CaMV35S), various actin gene promoters, various ubiquitin gene promoters, the nopaline synthase gene promoter, the tobacco PR1a gene promoter, promoters for the tomato ribulose-1,5-bisphosphate carboxylase-oxidase small subunit gene, and napin gene promoters. As indicated below, promoters are also preferred that have a lower expression strength than the 35S promoter, e.g., the promoter for *Arabidopsis thaliana* sigma factor SIG2 (AtSIG2).

When an expression vector capable of expressing a gene encoding the present protein is supplied to the cells of an organism, the action of the present protein may be brought about through the induction of expression of the present protein in the cells of the organism. Proceeding in this manner makes it possible to cause the expression of the action of the present protein according to an intended timing. Such an inducible promoter can be exemplified by inducible promoters that are induced by exogenous conditions, e.g., chemical substances or their concentrations, heat, or osmotic pressure, as well as by site-specific promoters and timing-specific promoters. These inducible promoters are selected as appropriate from known promoters, for example, the DEX promoter and HSP18.2 promoter, or the like.

In addition to a promoter and the aforementioned restriction enzyme gene, the expression vector may suitably contain other DNA segments. There are no particular limitations on these other DNA segments, and they can be exemplified by terminators, selection markers, enhancers, and base sequences for increasing the translation efficiency. In addition, the recombinant expression vector may also have a T-DNA region. The T-DNA region can increase the efficiency of gene introduction when in particular the recombinant expression vector is introduced into a plant body by using *Agrobacterium*.

As long as the transcription terminator is able to function as a transcription termination site, it is not otherwise particularly limited and may be a known transcription terminator. In specific terms, for example, transcription termination region of the nopaline synthase gene (Nos terminator), transcription termination region of cauliflower mosaic virus 35S (CaMV35S terminator), and so forth are preferably used. Among these, the use of the Nos terminator is more preferred.

Otherwise, appropriate selections of known elements can be used for the selection marker and the base sequences that increase the translation efficiency. There are also no particular limitations on the method for constructing the expression vector, and the required elements may be appropriately inserted in an appropriately selected parent vector.

Such an expression vector is introduced into a plant cell so as to cause the transient expression or constant expression of the present protein. In order to bring about the transient protein expression, the expression vector is physically introduced into the plant cell as, for example, a plasmid, using, for example, the PEG method, electroporation method, or particle gun method. In order to bring about constant expression, insertion into the plant genome is carried out by using, for example, the *Agrobacterium* method.

The use of the *Agrobacterium* method is advantageous from the standpoint of ensuring genome set diversity because it can lower the mortality rate of the plant cell caused by the introduction of the gene encoding the present protein. In addition, the *Agrobacterium* method is preferably applied to dicots and in particular to *Arabidopsis thaliana*.

Heretofore known methods can be used for the method of regenerating a plant body from, transformed plant cells.

In addition, in order to bring about the expression of the present protein in a cell, e.g., yeast, an expression vector adapted to yeast may similarly be constructed and introduced into the yeast. The expression vector can be constructed by the individual skilled in the art using a known method and a suitable enhancer in addition to a promoter and terminator. The expression cassette may also be configured in a chromosome-introduced form or may be configured in a form that is maintained outside the chromosome.

With regard to the construction of the expression vector, the use is preferred of an inducible promoter that enables the timing of protein expression to be intentionally determined. In addition, in order to establish the expression strength at a desired level, other control regions, e.g., promoter, terminator, and so forth, are also established as appropriate.

For example, the inducible promoter used can be a galactose-inducible promoter, e.g., GAL1 or GAL10, a promoter used in an induction system based on induction/removal due to an addition of doxycycline, e.g., the Tet-on system/Tet-off system, and promoters for genes that encode a heat shock protein (HSP), e.g., HSP10, HSP60, and HSP90; however, the use of the CUP1 promoter, which is activated by the addition of copper ion, is preferred. By using the CUP1 promoter, the cell can be cultured on a medium containing a carbon source such as glucose but lacking the copper ion, and subsequent to this expression of the double-stranded DNA breakage enzyme can be induced by culture with the addition to the medium of a copper ion compound. The concentration of the added copper ion can be established as appropriate; for example, it can be about at least 50 uM (micrometers) and not more than 300 uM. In addition, the culture time can be about 1 to 6 hours. Moreover, in order to avoid activation of the double-stranded DNA breakage enzyme at the same time as the induction of expression, the cell is preferably cultured at a temperature (for example, about 25 deg C.) that does not correspond to the activation conditions for the double-stranded DNA breakage enzyme. The CUP1 promoter is advantageous in that it enables the simple, convenient, and rapid intentional induction of expression and activation of the double-stranded DNA breakage enzyme.

The transformation of yeast by the introduction into yeast of such an expression vector so it is maintained intrachromosomally or extrachromosomally can be executed by the individual skilled in the art based on heretofore known methods.

Otherwise, for the expression vector that expresses the present protein, the individual skilled in the art can use, in conformity with the type of organism used and the intended action conditions for the present protein, standard recombinant DNA technology (for example, refer to Molecular Cloning, Third Edition, 1.84, Cold Spring Harbor Laboratory Press, New York), e.g., methods using restriction enzymes and DNA ligase, for the recombination procedures (e.g., insertion of the nucleic acid of the present invention, the promoter, the selection marker gene, and so forth into the vector).

There are no particular limitations on the direct supply of the present protein to the cells of the organism, but preferably the organism or portion thereof and the present protein are supplied in a state in which the present protein has been dissolved in an aqueous medium, e.g., water or a buffer. By doing this, the protein can be efficiently supplied into the cells of the organism.

To supply the present protein into the cells of the organism, the organism and the thusly prepared solution, for example, are brought into contact by, e.g., coating, immersion, mixing, and so forth, while otherwise injection into the organism is also possible. There are no particular limitations on the supply temperature and conditions, but the optimal temperature for the double-stranded DNA breakage activity of the present protein is preferably not used. For example, when the optimal temperature for the double-stranded DNA breakage activity is about 37 deg C., the temperature during supply is preferably not more than 30 deg C. and is more preferably not more than 25 deg C. The mode of direct supply of the present protein is useful in those instances where the organism is a cell, tissue, or organ.

(Mode for Causing the Action of the Present Protein in a Cell of an Organism)

The mode for causing the action of the present protein in a cell of an organism is described in the following. In the description that follows, reference to within a cell of an organism does not place a particular limitation on the form of the organism. For example, when the organism is a plant body, the form of the plant body is not a consideration and means a cell, tissue, or organ for a portion of an individual plant, or a seed, seedling, or ensuing developed individual plant, or intracellular for a callus. When the organism is a microorganism such as yeast, the meaning is that the present protein is caused to act within the cells thereof.

In order to cause the action of the present protein within a cell of an organism, the present protein may be present within the cell, but is preferably controlled to a degree that enables modification of the genome while maintaining the growth capacity of the organism. Due to this, for example, the present protein is intentionally and/or temporarily caused to act. More preferably, the present protein is intentionally and temporarily caused to act. This is because the growth of the cell is affected by an excessive double-stranded DNA breakage by the present protein being caused to act continuously at or above a certain intensity.

In bringing about the action of the present protein within a cell of an organism, the induction of the expression of the present protein is preferably controlled by using, e.g., an inducible promoter, site-specific promoter, timing-specific promoter, and so forth. By inducing the expression of the present protein, the expression and action of the present protein within a cell can then be brought about with intentional timing or at a targeted site and induction can be stopped, or this action can be more or less reduced or stopped with the passage of a prescribed period of time. When an inducible promoter is used, e.g., a temperature is determined and/or a chemical substance is supplied to the cell as appropriate in correspondence to a type of promoter.

Control of the strength of expression of the present protein by, e.g., a promoter or terminator is also related to the strength of the action of the present protein within a cell. Accordingly, the promoter and so forth are preferably selected also considering the strength of expression provided by, e.g., the promoter and terminator used.

Depending on characteristics such as the optimal temperature of the present protein, in some cases it may also be useful to continuously maintain the expression of the present protein using a constitutive promoter. This is because, when a characteristic such as, a strong dependence on temperature is present, its double-stranded DNA breakage activity can then be satisfactorily controlled by controlling the temperature conditions as described below. In addition, it will also be useful in some instances to continuously (constitutively) cause expression at a low intensity.

In bringing about the action of the present protein in the cells of an organism, the present protein present in the cells can also be caused to act under the growth conditions as such for the organism, and the double-stranded DNA breakage activity of the present protein in the cells is preferably artificially activated. In addition, inactivation is preferably carried out after this. By proceeding in this manner, the action of the present protein can be brought about more speedily and more effectively. For this purpose, for example, the present protein can be activated according to an intended timing by the application to the present protein of temperature conditions that are in a vicinity of its optimal temperature. This method is also useful in the case of the procedure of directly supplying the present protein to a cell.

Since the present protein has its optimal temperature for double-stranded DNA breakage activity in the ordinary temperature region, the application of temperature conditions in the vicinity of this ordinary temperature region to activate the double-stranded DNA breakage activity of the present protein enables the effective manifestation of the double-stranded DNA breakage activity of the present protein while lowering the effects of the temperature conditions on the growth activity of the organism. More specifically, the level of action (strength of action) is lowered, e.g., the temperature of action and time of action of the present protein are reduced, and the adverse effects on the organism due to temperature and double-stranded DNA breakage activity can then be avoided or suppressed.

Here, in the vicinity of the ordinary temperature region can be a temperature range that includes the ordinary temperature region of the various aspects that have already been described. For example, the lower limit is preferably at least 10 deg C., more preferably at least 15 deg C., even more preferably at least 20 deg C., and still more preferably at least 25 deg C., and the upper limit is preferably not more than 47 deg C., more preferably not more than 45 deg C., and even more preferably not more than 42 deg C. This range is preferably at least 10 deg C. and not more than 47 deg C., more preferably at least 10 deg C. and not more than 45 deg C., even more preferably at least 15 deg C. and not more than 45 deg C., even more preferably at least 20 deg C. and not more than 42 deg C., and still more preferably at least 25 deg C. and not more than 42 deg C.

The action time also depends on the action temperature conditions and the optimal temperature for the present protein and can be, for example, about from at least several minutes to not more than 1 hour. From at least 10 minutes to not more than 50 minutes is preferred and from at least 15 minutes to not more than 45 minutes is more preferred. It can also be, for example, at least 1 hour and not more than 10 hours, preferably at least 1 hour and not more than 6 hours, even more preferably at least 1 hour and not more than 4 hours, and still more preferably at least 1 hour and not more than 3 hours.

These temperature conditions can be established as appropriate considering, for example, the optimal temperature of the present protein, the effect on the organism, and the degree of modification of the DNA.

In plants, for example, the modification step of causing the action of the present protein within a cell of an organism is executed for a prescribed period of time, in a state in which the present protein can act, preferably on unplanted seeds harvested from an organism that is a parent plant that has been transformed to enable expression of the present protein, or in the interval after planting and up to germination, or on seedlings post-germination, or on a more developed plant body. In addition, for example, in the case of yeast, expression of the present protein is caused, or activation is caused of the expressed present protein, in parent yeast that have been transformed to enable the expression of the present protein.

When the organism is a plant, one or two or more selections from the group consisting of seeds, the shoot apex, lateral buds, flower buds, pollen, ovaries, endosperm, embryo, and portions of the preceding are preferred for this modification step. This is because a more effective trait modification can be expected from modification of the genome of such plant bodies or portions thereof.

When the organism is a plant, the modification step can be exemplified by the incubation, in a state in which the present protein can act, of, e.g., the seed, seedling, or developed plant, for example, at a temperature condition of 37 deg C. for several tens of minutes to several hours, followed by return to the lower temperature growth conditions (for example, about 20 to 25 deg C. for *Arabidopsis thaliana*).

When the organism is a yeast, the mode can be exemplified by the maintenance, in a state in which the present protein can act, of the yeast culture conditions, for example, at 37 deg C. for about several tens of minutes to several hours, followed by return to the usual culture temperature (about 25 to 30 deg C.).

When the organism is an animal, the mode can be exemplified by the maintenance, in a state in which the present protein can act, of animal cells containing unfertilized eggs or fertilized eggs, for example, at 37 deg C. for about several tens of minutes to several hours, followed by the elimination of the action of the present protein (for example, cancelling the action of the promoter).

In order to establish the various conditions of action and selection of the present protein in this modification step, an evaluation step can be preliminarily carried out in which the functional state of the present protein is evaluated using a growth state of the organism (delay/inhibition of growth, lowering of the survival rate) as an indicator. This is because a delay or inhibition of organism growth or a decline in the survival rate of the organism is observed when genetic recombination is produced in the genome through the appearance of the double-stranded DNA breakage activity of the present protein. The present inventors have found that, even when this, e.g., growth inhibition, occurs, an effective genomic modification is still produced in the organism.

In addition to this evaluation step or in place of this evaluation step, an evaluation step may be carried out in which the functional state of the present protein is evaluated by indirectly detecting recombination in the organism. The indicator in such an evaluation step can be, for example, the increase in the extent of expression in the organism of a gene associated with DNA repair, for example, the BRCA1 gene, or the level of homologous recombination based on the GUS reporter gene. The execution of this evaluation step makes it possible to more specifically comprehend the degree of genetic recombination in the organism due to the action of the present protein.

Through the execution of this evaluation of the functional state of the present protein, the individual skilled in the art will be able to appropriately establish an organism and restriction enzyme that may be effectively used in the present modification method as well as the strength of action of the restriction enzyme and the conditions for its action.

Based on the above, the present disclosure also provides a method of evaluating a system for modifying a genome of an organism, wherein the evaluation method comprises:

causing an action, under one or two or more conditions, in a cell, of an organism of one or two or more proteins that have their optimal temperature for double-stranded DNA breakage activity in an ordinary temperature region; and evaluating a functional state of the protein by using a growth state of the organism or genetic recombination in the organism as an indicator of the functional state of the one or two or more proteins under the one or two or more conditions.

Based on the above, the present disclosure also provides a method of determining a protein and/or its action conditions for use in a system for modifying a genome of an organism, the method comprising:

causing the action, under one or two or more action conditions, in a cell of an organism of one or two or more proteins that have their optimal temperature for double-stranded DNA breakage activity in the ordinary temperature region; and evaluating the functional state of the protein using the growth state of the organism or genetic recombination in the organism as an indicator of the functional state of the one or two or more proteins under the one or two or more action conditions, wherein the protein and/or its action conditions for use in the system are determined based on the aforementioned evaluation.

The execution of this modifying makes it possible to produce genetic recombination in the genome and thereby obtain a genetically modified organism. Since a degree of genomic modification caused by the present protein varies from organism to organism, e.g., cells, to which the present protein is applied, a population of organisms having various different states of modification can be obtained as a result.

As has been described in the above, the present modification method—by causing the action in a cell of an organism of the present protein having its optimal temperature for double-stranded DNA breakage activity in the ordinary temperature region—makes possible an effective genomic modification and makes possible a reduction in the thermal load on the organism during the action of the present protein. As a result, traits associated with a plurality of genes, e.g., quantitative traits, can be efficiently enhanced.

The present modification method is itself a method of producing an organism that has a modified genome, and, through the application of such a modification step to a parent organism, it is also a method of producing a population of genomically modified organisms, and being able to provide a population of genomically modified organisms. In addition, by carrying out a step of selecting an intended eukaryotic organism from the thusly obtained population of organisms based on an indicator, it is also a method of producing an organism having modified characteristics that enables the acquisition of an organism corresponding to the intention.

(Breeding Material)

The breeding material according to the present disclosure comprises DNA that has a coding region that codes for a protein that has its optimal temperature for double-stranded DNA breakage activity in the ordinary temperature region, and this coding region can contain an intron that is not processed within the host for the breeding material. Due to the presence of this intron within this breeding material, the mature protein having double-stranded DNA breakage activity is not synthesized. The result of this is to suppress or prevent a reduction in the growth activity of the host carrying this DNA that would be caused by the double-stranded DNA breakage activity developed by the mature protein.

The intron is constituted such that it is processed in the eukaryotic organism where the action of the protein is intended.

This breeding material can be various known expression vectors for eukaryotic organisms. The expression vector is generally maintained and amplified in a suitable host. The present breeding material can be reliably maintained and amplified even in a prokaryotic host that is a prokaryotic microorganism, e.g., *E. coli*.

There are no particular limitations on the intron used in the present breeding material, and already known introns of the known coding regions for proteins in eukaryotic organisms can be used as appropriate.

EXAMPLES

Examples that realize the present disclosure are described in the following. These examples describe the present disclosure but do not limit its scope.

Example 1

(1) Construction of a Plant Expression Vector for the HinP1I Gene and MseI Gene

The sequences registered in Genbank were consulted for the base sequences for the HinP1I gene and MseI gene (HinP1I gene base sequence: AY849924, MseI gene base sequence: DQ356003). *Arabidopsis thaliana* codon optimization was carried out on these sequences; the intron sequence derived from castor bean catalase (Ma et al., 2011, Plant Science 181, 188-194) was then inserted; and artificially synthesized genes were designed in which the FLAG tag sequence was ligated at the 5'-end and a nucleus localization signal (NLS) sequence was ligated at the 3'-end. These artificially synthesized genes are designated FLAG-iHinP1I-NLS and FLAG-iMseI-NLS in the following (FIG. 1).

The following plant expression vectors for these artificially synthesized genes were used: pBI HSP18.2: FLAG-iHinP1I-NLS and pBI HSP18.2: FLAG-iMseI-NLS, in which the gene of interest was located downstream of the HSP18.2 promoter, and pBI DEX: FLAG-iHinP1I-NLS and pBI DEX: FLAG-iMseI-NLS, in which the gene of interest was located downstream of the DEX inducible promoter (indicated as DEX in the following).

Example 2

(2) Introduction of the Gene of Interest into *Arabidopsis thaliana*

Using *Agrobacterium* carrying pBI HSP18.2: FLAG-iHinP1I-NLS or pBI HSP18.2: FLAG-iMseI-NLS or pBI DEX: FLAG-iHinP1I-NLS or pBI DEX: FLAG-iMseI-NLS, each gene was introduced into *Arabidopsis thaliana* strain 1406 (EMBO Journal (2006) 25, 5579-5590).

The strain 1406 is constructed by the insertion of a GUS reporter gene having an inverted repeat structure into strain Col-0, such that the GUS gene is expressed when homologous recombination is produced within the GUS gene. It is used in the quantitative analysis of homologous recombination based on this arrangement. An in planta method was used for the transformation method. Seeds recovered after *Agrobacterium* infection were planted in MS agar medium containing kanamycin (Murashige-Skoog inorganic salts, 1% sucrose, 0.05% MES, 0.8% agar, 50 mg/L kanamycin sulfate). After growth for 2 weeks in a climate controlled room at 22 deg C. using a 16-hour light period/8-hour dark period and a light intensity of about 30 to 50 umol (micromole)/m²/sec, the kanamycin-resistant individuals were selected to obtain the transformants.

Example 3

(3) Observation of growth for the plant bodies incorporating the DEX: FLAG-iHinP1I-NLS gene or DEX: FLAG-iMseI-NLS (DEX: iHinP1I transgenic strain or DEX: iMseI transgenic strain)

Seeds from each of the DEX: iHinP1I transgenic strain, the DEX: iMseI transgenic strain, and a transformant strain that constantly expressed TaqI, a heat-resistant high-frequency restriction enzyme (TaqI-ox, Japanese Patent Application Publication No. 2011-160798), were planted in MS agar medium containing kanamycin (Murashige-Skoog inorganic salts, 1% sucrose, 0.05% MES, 0.8% agar, 50 mg/L kanamycin sulfate). After incubation for 2 weeks in a climate controlled room at 22 deg C. using a 16-hour light period/8-hour dark period and a light intensity of about 30 to 50 umol/m$^2$/sec, the growth status was inspected. Growth of the individual plants was inhibited for the DEX: iHinP1I transgenic strain and the DEX: iMseI transgenic strain (FIG. 2).

Example 4

(4) 1-4 Gene Expression Analysis for the DEX: iHinP1I Transgenic Strain and the DEX: iMseI Transgenic Strain Total RNA extraction from the plant body used in the analysis in (3) was performed using an RNeasy Plant Mini Kit (Qiagen), and a reverse transcription reaction was then run using a High-Capacity RNA-to-cDNA Kit (Life Technologies Corporation) to prepare cDNA. The expression of the 18SrRNA and BRCA1 genes was subsequently analyzed by real-time PCR (ABI PRISM 7300) using Power SYBR Green PCR Master Mix (Life Technologies Corporation). In a comparison among the individual samples using 18SrRNA as the internal control, the analysis was performed by calculating the relative amount of expression from (value of the BRCA1 signal)/(value of the 18SrRNA signal). The results are given in FIG. 3.

The primers used in the expression analysis are as follows.

18SrRNA-F: CGGCTACCACATCCAAGGAA (SEQ ID NO: 01)

18SrRNA-R: TGTCACTACCTCCCCGTGTCA (SEQ ID NO: 02)

BRCA1-F: CCATGTATTTTGCAATGCGTG (SEQ ID NO: 03)

BRCA1-R: TGTGGAGCACCTCGAATCTCT (SEQ ID NO: 04)

Figure 3:
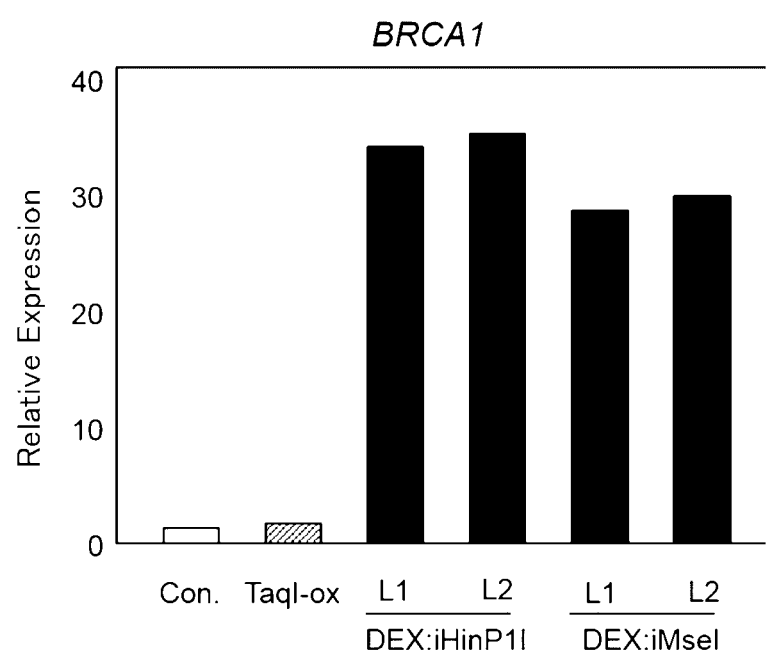
FIG. 3 is a graph that shows increases in expressions of the BRCA1 gene, a genomic double-stranded break repair factor, in a plant that expresses the ordinary-temperature restriction enzyme, under normal growth conditions.

As shown in FIG. 3, under normal growth conditions (22 deg C.), BRCA1 expression was about the same in the TaqI-expressing strain as in the control, while in the ordinary-temperature restriction enzyme-expressing strains it was increased several 10-fold. BRCA1 is known to be an important factor in the repair of genomic double-stranded breakage (West, C. E., et al. "*Arabidopsis* DNA double-strand break repair pathways." Biochemical Society Transactions 32.6 (2004): 964-966), and it was thus indicated that, in the ordinary-temperature restriction enzyme-expressing strains, the plant genome had undergone high-frequency genomic breakage and genomic rearrangement had been induced.

Example 5

(5) Analysis of GU-US Gene Rearrangement in the DEX: iHinP1I Transgenic Strain and the DEX: iMseI Transgenic Strain The plant bodies used in the analysis in (3) were subjected to GUS staining. The GUS staining was basically according to the method of Kim et al. (Kim et al., 2006). First, 90% acetone was dispensed into a tube and was pre-chilled to 4 deg C. The plant body to be observed was immersed in the 90% acetone and standing on ice was carried out until sampling was finished. After all the sampling was finished, standing was carried out for twenty minutes at room temperature. During this interval, the tube was turned over two or three times and the acetone solution and samples were gently stirred.

After this, rinsing was performed three times with 50 mM phosphate buffer (pH 7.0), followed by substitution to X-Gluc solution (1.9 mM X-Gluc (5-bromo-4-chloro-3-indolyl-Beta-D-glucuronide cyclohexylammonium salt), 0.5 mM $K_3Fe(CN)_6$, 0.5 mM $K_4[Fe(CN)_6]$-$3H_2O$, 0.3% Triton X-100, 50 mM phosphate buffer (pH 7.0)).

The sample was then depressurized at a pressure of 0.075 MPa (5 seconds, 2 times) and the X-Gluc solution was infiltrated into the sample followed by standing for from 2 hours to overnight at 37 deg C. The stained tissue presents a blue color. Once staining had been confirmed, the staining reaction was stopped by substitution with 70% EtOH and the chlorophyll and the like was also bleached. Each of the GUS-stained plant bodies was observed with a stereomicroscope, and the number of blue spots originating with the expression of the GUS gene produced due to rearrangement of the GU-US gene was measured on each plant body. The results are given in FIG. 4.

Figure 4:
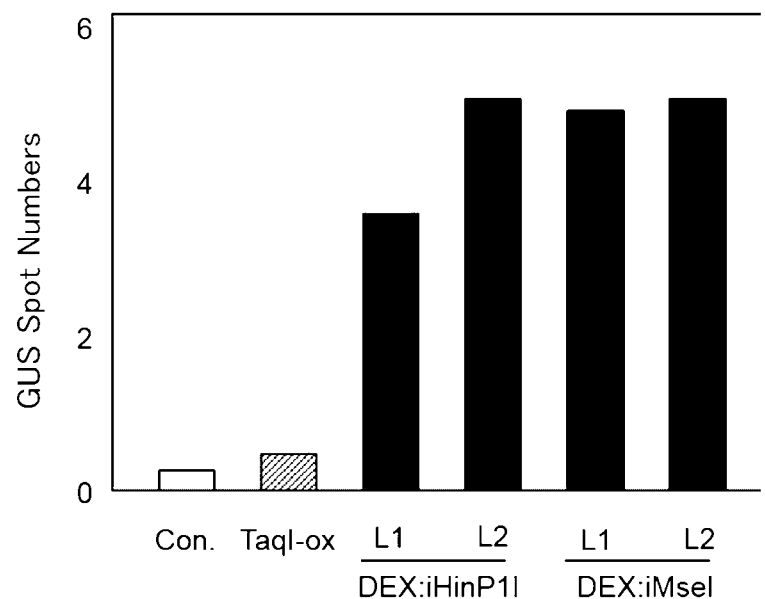
FIG. 4 is a diagram that shows increases in a small-scale rearrangement frequency under normal growth conditions in a plant that expresses the ordinary-temperature restriction enzyme.

As shown in FIG. 4, under the normal growth conditions (22 deg C.), with the TaqI-expressing strain the number of GUS spots was about the same as the control, while with the ordinary-temperature restriction enzyme-expressing strains the number of spots was increased about 4-fold.

Considered together with the increase in the expression of the BRCA1 gene, which is a factor that repairs genomic double-strand breaks, this indicated that genomic rearrangement could be induced in the ordinary temperature region (temperature region in which the plant normally grows) by the expression in the plant cells of the ordinary-temperature restriction enzyme. On the other hand, in the transgenic strains that were analyzed at this time, the possibility exists that genomic rearrangement is induced by the constant expression of the ordinary-temperature restriction enzyme to a degree that exercises an effect on plant growth. It is thought that, by constructing an expression induction system that exhibited a little expression leakage, the effects on plant growth could be restrained and genomic rearrangement could be induced at will at high efficiencies.

Example 6

(6) Observation of Growth for the Plant Bodies Incorporating the HSP18.2: FLAG-iHinP1I-NLS Gene or HSP18.2: FLAG-iMseI-NLS Gene (HSP18.2: iHinP1I Transgenic Strain or HSP18.2: iMseI Transgenic Strain)

Seeds from each of the HSP18.2: iHinP1I transgenic strain, the HSP18.2: iMseI transgenic strain, and the TaqI-ox strain were planted in MS agar medium (Murashige-Skoog inorganic salts, 1% sucrose, 0.05% MES, 0.8% agar). The growth status was inspected after incubation for 2 weeks in a climate controlled room at 22 deg C. using a 16-hour light period/8-hour dark period and a light intensity of about 30 to 50 umol/m²/sec (normal growth conditions). The results are given in FIG. 5.

Figure 5:
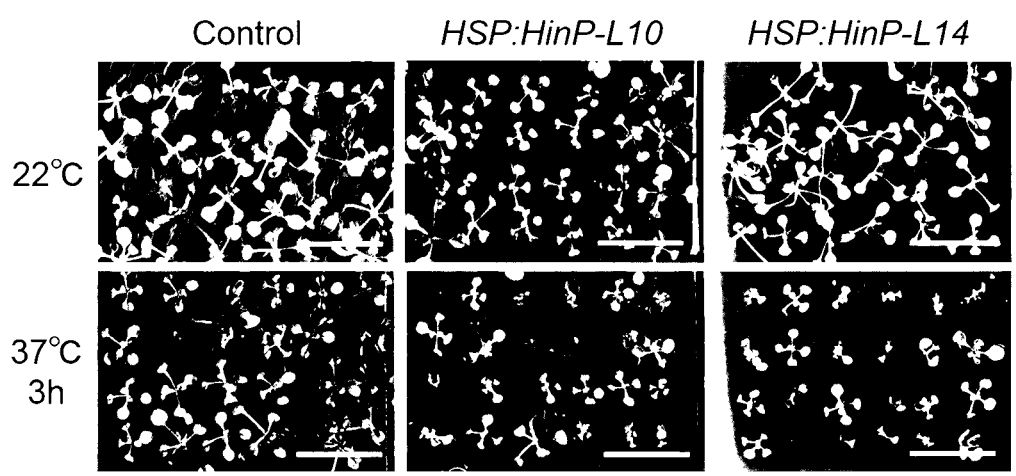
FIG. 5 is a photo that shows delays in seedling plant growth due to induction of the expression of the ordinary-temperature restriction enzyme.

As shown in FIG. 5, a significant difference in the growth of the individual plants was not seen between the control plants and the HSP18.2: iHinP1I transgenic strain, the HSP18.2: iMseI transgenic strain, or the TaqI-ox strain. Based on the suppression of effects on plant growth, it is thought that an expression induction system that exhibited a little expression leakage had been constructed.

In addition, when each strain was incubated under the normal growth conditions for 1 week after planting, was then subjected to a heat treatment for 3 hours at 37 deg C. and a light intensity of about 30 to 50 umol/m²/sec, and was thereafter incubated for an additional 1 week under the normal growth conditions, delayed growth was seen with the HSP18.2: iHinP1I transgenic strain and the HSP18.2: iMseI transgenic strain as shown in FIG. 5. This indicated that high-frequency breakage of the plant genome had been induced by the induction of the expression of the ordinary-temperature restriction enzymes in the HSP18.2: iHinP1I transgenic strain and the HSP18.2: iMseI transgenic strain.

Example 7

(7) Gene Expression Analysis for the HSP18.2: iHinP1I Transgenic Strain and the HSP18.2: iMseI Transgenic Strain From among the plant bodies used in the analysis in (6), the strains incubated under the normal growth conditions for 1 week after planting and the HSP18.2: iHinP1I transgenic strain and the HSP18.2: iMseI transgenic strain after incubation under the normal growth conditions for 1 week after planting, were subjected to a heat treatment for 3 hours at 37 deg C., while the TaqI-ox strain was subjected to a heat treatment for 24 hours at 37 deg C.; this was followed by sampling. Total RNA extraction was performed from each sample using an RNeasy Plant Mini Kit (Qiagen), and a reverse transcription reaction was then run using a High-Capacity RNA-to-cDNA Kit (Life Technologies Corporation) to prepare cDNA. The expression of the 18SrRNA and BRCA1 genes was subsequently analyzed by real-time PCR (ABI PRISM 7300) using Power SYBR Green PCR Master Mix (Life Technologies Corporation). The results are given in FIG. 6.

Figure 6:
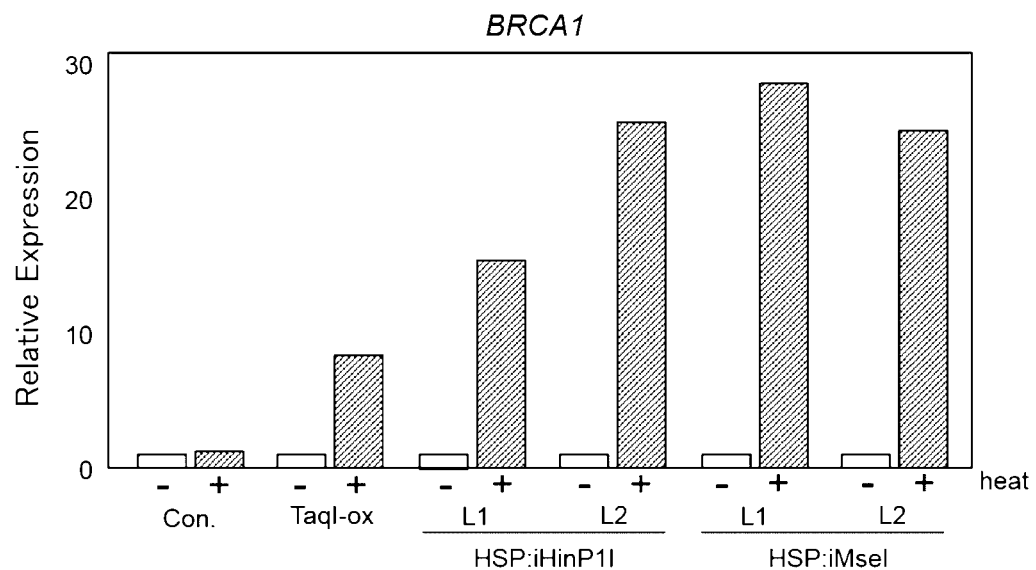
FIG. 6 is a graph that shows increases in the expression of the BRCA1 gene, the genomic double-stranded break repair factor, due to the induction of the expression of the ordinary-temperature restriction enzyme.

As shown in FIG. 6, at the normal growth conditions (22 deg C.), BRCA1 expression in the TaqI-ox strain, the HSP18.2: iHinP1I transgenic strain, and the HSP18.2: iMseI transgenic strain was about the same as in the control. An increase was seen in the expression of the BRCA1 gene in the TaqI-ox strain due to the heat treatment of 24 hours at 37 deg C., but with the HSP18.2: iHinP1I transgenic strain and the HSP18.2: iMseI transgenic strain a higher BRCA1 expression than in the TaqI-ox strain was induced by the heat treatment of 3 hours at 37 deg C. It was confirmed that, at one-eighth the heat treatment time, the genomic rearrangement induction effect was higher than for the conventional TaqI-expressing strain.

Example 8

(8) Analysis of GU-US Gene Rearrangement in the HSP18.2: iHinP1I-Expressing Strain and the HSP18.2: iMseI-Expressing Strain A GUS staining experiment was run on the plant bodies used in the analysis in (6) in order to analyze GU-US gene rearrangement. The representative results are given in FIG. 7.

Figure 7:
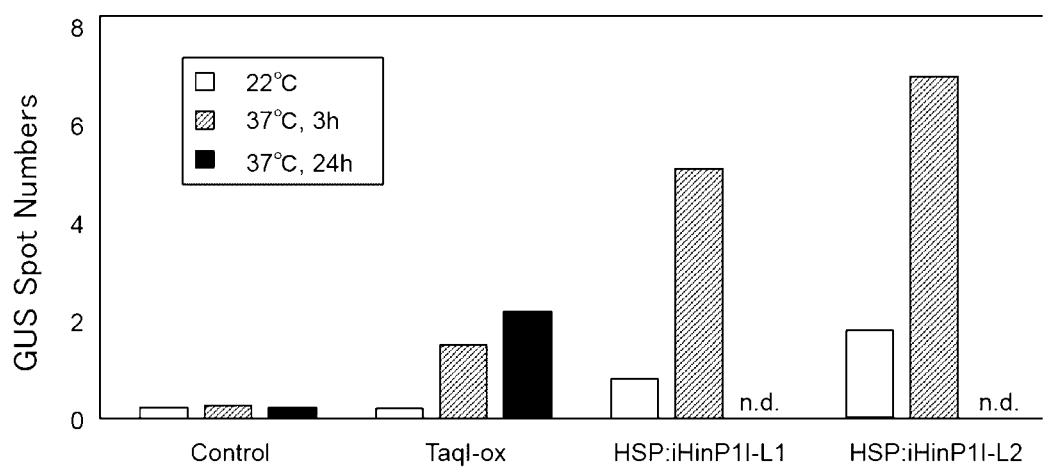
FIG. 7 is a graph that shows increases in the small-scale rearrangement frequency due to the induction of the expression of the ordinary-temperature restriction enzyme.

As shown in FIG. 7, an increase in the number of GUS spots due to the 24 hour/37 deg C. heat treatment was seen with the TaqI-ox strain, but in the HSP18.2: iHinP1I transgenic strain the number of GUS spots was increased over that for the TaqI-ox strain even by the 3 hour/37 deg C. heat treatment. The numbers of GUS spots were also increased by 3 hours/37 deg C. heat treatment in HSP18.2: iMseI transgenic strains. Accordingly, it is concluded that genomic rearrangement could be realized in the ordinary-temperature restriction enzyme-expressing strains at a higher frequency than in the TaqI-ox strain by a milder heat treatment (at least about ⅛th) than heretofore.

Example 9

(9) Observation of flower stalk growth in the HSP18.2: iHinP1I transgenic strain and the seeds from the HSP18.2: iHinP1I transgenic strain and the HSP18.2: iMseI transgenic strain—was planted in MS agar medium (Murashige-Skoog inorganic salts, 1% sucrose, 0.05% MES, 0.8% agar). Incubation was carried out for 2 weeks in a climate controlled room at 22 deg C. using a 16-hour light period/8-hour dark period and a light intensity of about 30 to 50 umol/m²/sec (normal growth conditions), followed by transplantation to a soil mix and incubation under normal growth conditions for 4 weeks. Incubation was carried out for 1 week under normal growth conditions after a 3 hour/37 deg C. heat treatment and plant growth was then inspected. The representative results are given in FIG. 8.

Figure 8:
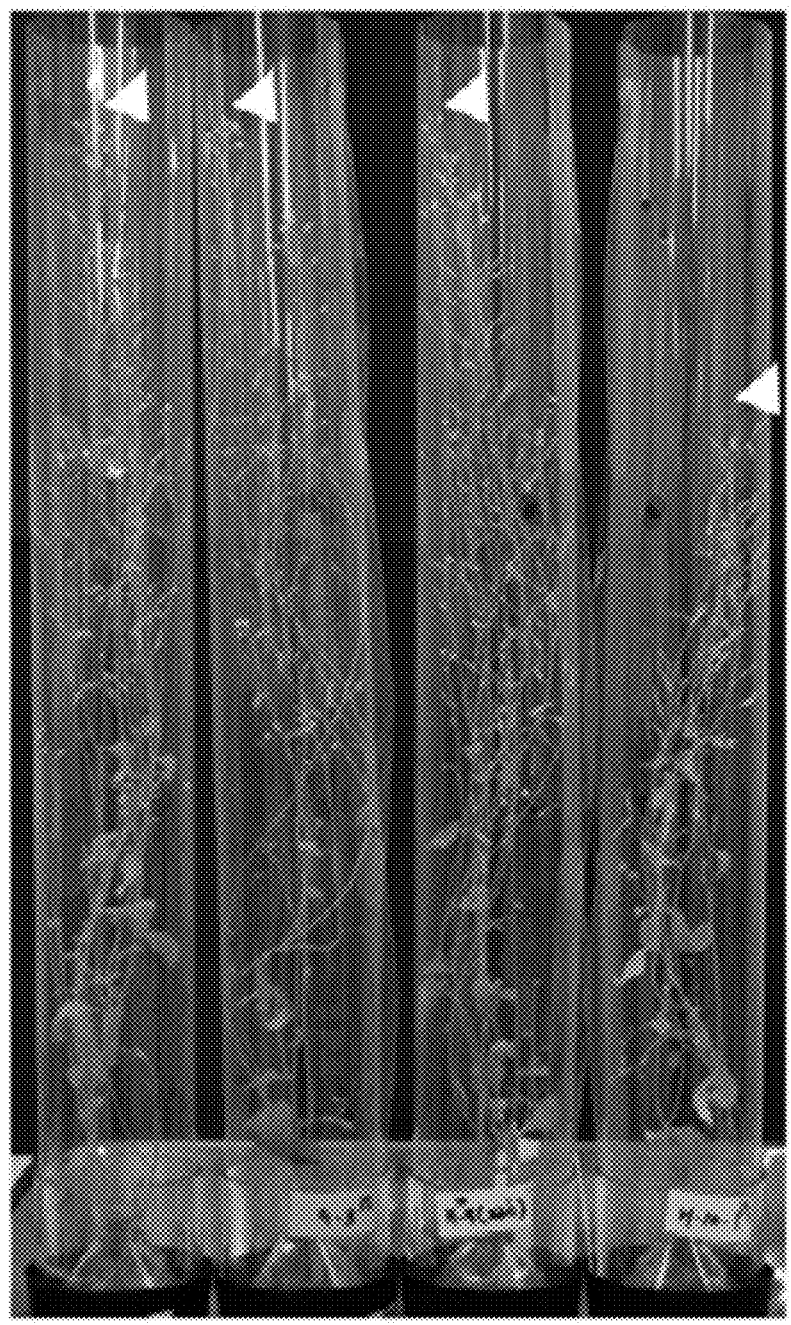
FIG. 8 is a photograph that shows a delay in growth of the flower stalk due to the induction of the expression of the ordinary-temperature restriction enzyme.

As shown in FIG. 8, a delay in growth was confirmed for the heat-treated HSP18.2: iHinP1I transgenic strains. These phenomena were also confirmed for the heat treated HSP18.2: iMseI transgenic strains. This indicated that breakage of the plant genome was induced in the ordinary-temperature restriction enzyme-expressing strains by heat treatment at a level that did not exercise an effect on the fertility of the control plants.

Example 10

(10) Expression Analysis in Flower Stalks for the HSP18.2: iHinP1I Transgenic Strain and the HSP18.2: iMseI Transgenic Strain From the plants used in the analysis in (9), flower buds and cauline leaves were each sampled from the plants immediately after carrying out the 3 hour/37 deg C. heat treatment. Total RNA extraction from each sample was performed using an RNeasy Plant Mini Kit (Qiagen), and a reverse transcription reaction was then run using a High-Capacity RNA-to-cDNA Kit (Life Technologies Corporation) to prepare cDNA. The expression of the 18SrRNA and BRCA1 genes was subsequently analyzed by real-time PCR (ABI PRISM 7300) using Power SYBR Green PCR Master Mix (Life Technologies Corporation). The results are given in FIG. 9.

Figure 9:
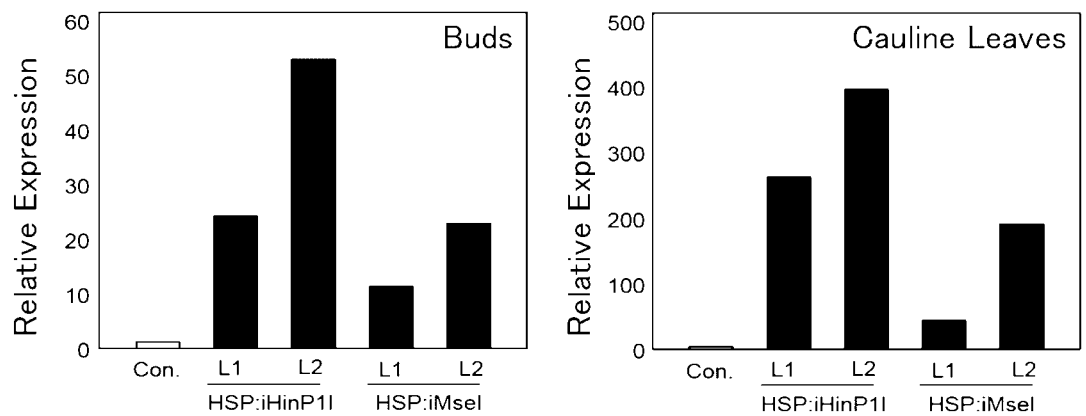
FIG. 9 is a graph that shows increases in the expression of the BRCA1 gene, the genomic double-stranded break repair factor, in flower buds and cauline leaves due to the induction of the expression of the ordinary-temperature restriction enzyme.

As shown in FIG. 9, for both the HSP18.2: iHinP1I transgenic strain and the HSP18.2: iMseI transgenic strain, BRCA1 expression was increased by the 3 hour/37 deg C. heat treatment in both organs, i.e., the flower buds and cauline leaves, by several 10-fold to several 100-fold over the control plants. This indicated that plant genome rearrangement was induced by the induction of the expression of the ordinary-temperature restriction enzymes by heat treatment at a level that did not exercise an effect on the fertility of the control plants.

Example 11

Figure 10:
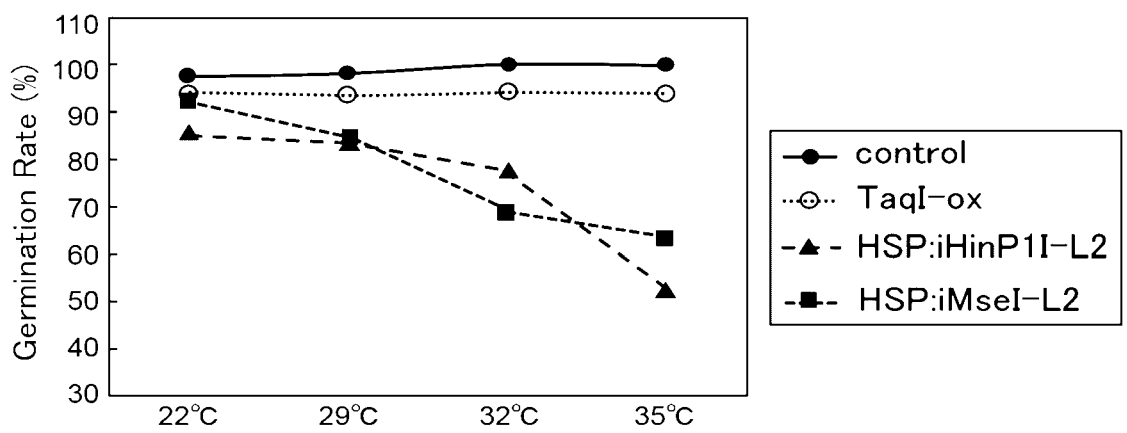
FIG. 10 is a graph that shows delays in growth of post-emergence seedlings due to the induction of the expression of the ordinary-temperature restriction enzyme.

(11) Observation of Growth for Hydrated Seeds for the HSP18.2: iHinP1I Transgenic Strain and the HSP18.2: iMseI Transgenic Strain Seeds from each of the HSP18.2: iHinP1I transgenic strain and the HSP18.2: iMseI transgenic strain were sterilized and were incubated (heat treatment) for 1 hour in warm water (29 deg C., 32 deg C., and 35 deg C.) and were then planted in MS agar medium (Murashige-Skoog inorganic salts, 1% sucrose, 0.05% MES, 0.8% agar). After incubation for 4 days in a climate controlled room at 22 deg C. using a 16-hour light period/8-hour dark period and a light intensity of about 30 to 50 umol/m$^2$/sec (normal growth conditions), the individuals that had developed greened cotyledons were counted and this was used as the germination rate. With the HSP18.2: iHinP1I transgenic strain and the HSP18.2: iMseI transgenic strain, the germination rate under the heat treatment conditions was retarded in comparison to the control plants. Also with regard to the seeds, a retardation of germination by the heat treatment was not seen with the TaqI-ox strain, for which the induction of expression of the ordinary-temperature restriction enzyme and the development of genomic rearrangement were indicated (FIG. 10). The induction of genomic rearrangement in the seed has not been confirmed for strains that express a heat-resistant high-frequency restriction enzyme, most prominently TaqI. The induction of genomic rearrangement with the seed was shown to be possible with the ordinary-temperature restriction enzyme-expressing strains developed by us at this time.

Example 12

(12) Survival Rate for Ordinary-Temperature Restriction Enzyme Expression in Yeast The effect of the expression of ordinary-temperature restriction enzymes on growth was analyzed using *Saccharomyces cerevisiae*. PCR reactions were carried out using the following oligoDNAs and the FLAG-iHinp1I-NLS gene and FLAG-iMseI-NLS gene fragments were recovered.

```
iHinP1I-F:
                                        (SEQ ID NO: 05)
CATAAAATATTCAGCGAATTGGATCCATGGATTACAAGGACGATGATG iHinP1I-R:
                                        (SEQ ID NO: 06)
GATGGTGATGCGATCCTCTCTGCAGTCAACCTCCAACCTTCCTCTTCTT iMseI-F:
                                        (SEQ ID NO: 07)
CATAAAATATTCAGCGAATTGGATCCATGGATTACAAGGACGATGATGA iMseI-R:
                                        (SEQ ID NO: 08)
GATGGTGATGCGATCCTCTCTGCAGTCAACCTCCAACCTTCCTCTTCTT
```

Each of the gene fragments was inserted into the pORF-CLONE vector (MoBiTec), which supports the induction of expression by the addition of copper ion. The fabricated plasmid vectors were designated pORF-CLONE-FLAG-iHinp1I-NLS and pORF-CLONE-FLAG-iMseI-NLS. pORF-CLONE-FLAG-iHinp1I-NLS, pORF-CLONE-FLAG-iMseI-NLS, and pORF-CLONE as control were introduced into strain YPH499 (S288C), thus providing pORF-CLONE-FLAG-iHinp1I-NLS/YPH499, pORF-CLONE-FLAG-iMseI-NLS/YPH499, and pORF-CLONE//YPH499. Culture was carried out for 24 hours at 30 deg C. using a minimal medium commonly used for the culture of yeast transformants (SD-LEU medium (2% glucose, 0.67% yeast nitrogen base, 0.69 g/L CSM-LEU)). The expression of the FLAG-iHinp1I-NLS gene and FLAG-iMseI-NLS gene was induced by the addition of 150 μM copper sulfate and culture for 4 hours at 30 deg C. The cells were then washed with sterile MilliQ water and subsequently brought to 5×10$^5$ cells/mL with sterile MilliQ water and were hot incubated for 30 minutes at 30 deg C. or 42 deg C. After the heat treatment, the cells were quickly transferred onto ice and were plated to YPD plates and cultured for 2 days at 30 deg C. and the survival rate was then measured. The results are given in FIG. 11.

Figure 11:
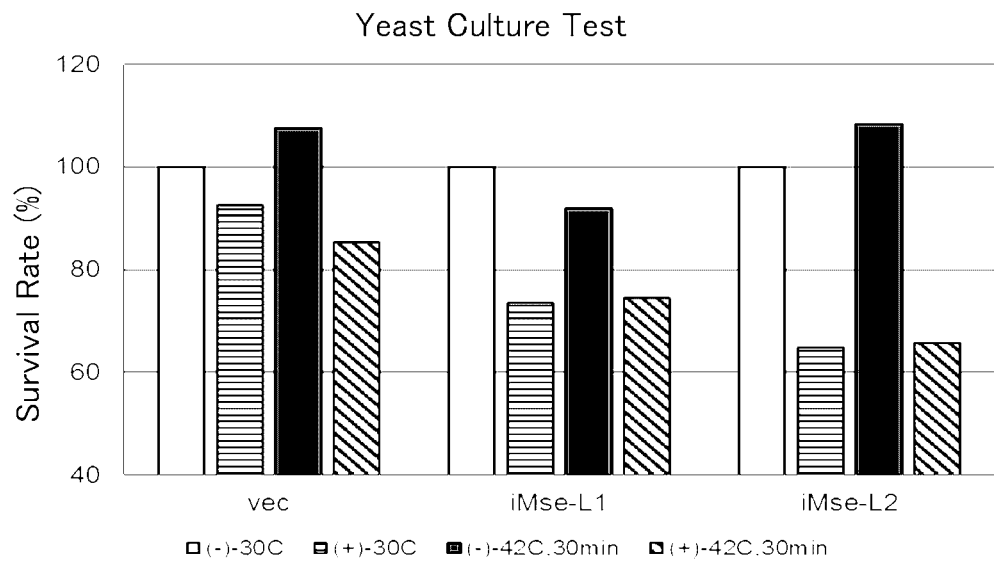
FIG. 11 is a graph that shows declines in a survival rate of yeasts due to the expression of the ordinary-temperature restriction enzyme.

As shown in FIG. 11, it was found that, regardless of the presence/absence of the hot incubation after copper ion induction, the survival rate was lowered in the ordinary-temperature restriction enzyme-expressing yeast (L1 and L2) in comparison to the control yeast (pORF-CLONE/YPH499, vec) into which an empty vector had been introduced. In previous development to date, the survival rate in TaqI-expressing yeast has been reduced in a high temperature-dependent manner. It was indicated that an effect on yeast growth due to DNA breakage was exercised due to the excision of the plant-type intron within the yeast and the expression of the ordinary-temperature restriction enzyme MseI.

Example 13

(13) Results for a Yeast Intron-Incorporating Ordinary-Temperature Restriction Enzyme PCR reactions were carried out using pBI HSP18.2: FLAG-iMseI-NLS as the template and using the following oligoDNAs to fabricate the artificial gene iMseI(RUB1) which incorporated an intron sequence derived from the yeast RUB1 gene.

```
NT123:
                                        (SEQ ID NO: 9)
AGATCTATGGATTACAAGGACGATGA

NT124:
                                        (SEQ ID NO: 10)
GAGCTCTCAACCTCCAACCTTCCTCT

NT125:
                                        (SEQ ID NO: 11)
GTAAAATCGGTTAATTTCCCCTTTCTTTCTTTTCCTCACTCCGAAGTGTA
CATACCTTTTCACTCTGAGTCC

NT127:
                                        (SEQ ID NO: 13)
AGGTCTCAAAAACGTAAATAAACTTAAAAGATAATTAACCACTGAATGAA
CATACCTTTTCACTCTGAGTCCCTT
```

In addition, PCR reactions were carried out on pBI HSP18.2: FLAG-iMseI-NLS using the following oligoDNAs to fabricate the artificial gene iMseI(CNB1) which incorporated an intron sequence derived from the yeast CNB1 gene.

```
NT123:
                                        (SEQ ID NO: 9)
AGATCTATGGATTACAAGGACGATGA
```

-continued

NT124:
(SEQ ID NO: 10)
GAGCTCTCAACCTCCAACCTTCCTCT

NT126:
(SEQ ID NO: 12)
GAAAAGAAAGAAAGGGGAAATTAACCGATTTTACTAACACTGACACTTTG

AACAGGTCTGGATCTTCTGATGCTG

NT128:
(SEQ ID NO: 14)
TAATTATCTTTTAAGTTTATTTACGTTTTTGAGACCTTACTAACGACCAG

GATAGGTCTGGATCTTCTGATGCTG

Each of the gene fragments was inserted in the prtTA-pCMV-pCYC1-kanMX vector, which supports the induction of expression by doxycycline. The constructed plasmid vectors were designated prtTA-pCMV-pCYC1-iMseI(RUB1)-kanMX and prtTA-pCMV-pCYC1-iMseI(CNB1)-kanMX. prtTA-pCMV-pCYC1-iMseI(RUB1)-kanMX, prtTA-pCMV-pCYC1-iMseI(CNB1)-kanMX, and prtTA-pCMV-pCYC1-kanMX as control were inserted into strain YPH499 (S288C lineage) to produce YPH499/prtTA-pCMV-pCYC1-kanMX, YPH499/prtTA-pCMV-pCYC1-iMseI(RUB1)-kanMX, and YPH499/prtTA-pCMV-pCYC1-iMseI(CNB1)-kanMX.

The transformants were cultured for 24 hours at 25 deg C. on SD/MSG+G418 medium (2% glucose, 0.17% yeast nitrogen base w/o amino acid, 0.1% monosodium glutamic acid, 10 mg/L adenine, 50 mg/L L-arginine, 50 mg/L L-aspartic acid, 20 mg/L L-histidine, 50 mg/L L-isoleucine, 100 mg/L L-leucine, 50 mg/L L-lysine, 20 mg/L L-methionine, 50 mg/L L-phenylalanine, 100 mg/L L-threonine, 50 mg/L L-tryptophan, 50 mg/L tyrosine, 20 mg/L uracil, 140 mg/L valine, 200 mg/L G418).

Gene expression was induced by the addition of 10 uM doxycycline and culture for 5 hours at 25 deg C. The cells were washed in sterile MilliQ water and then suspended in sterile MilliQ water. A hot incubation was carried out for 60 minutes at 25 deg C. or 37 deg C. The cells were diluted and plated to YPD plates and cultured for 3 days at 25 deg C. and the survival rate was then measured. The results are given in FIG. 12.

Figure 12:
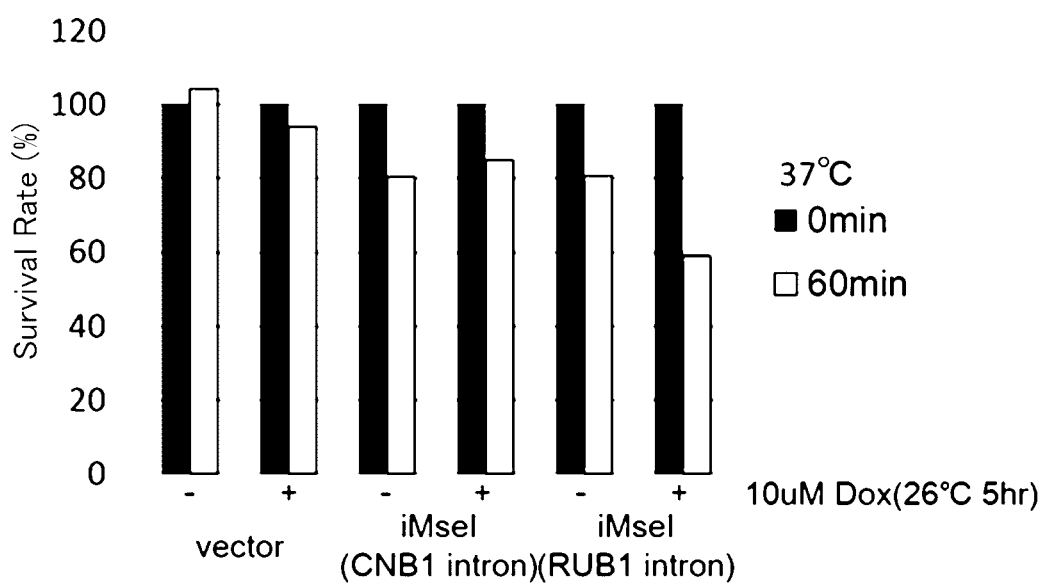
FIG. 12 is a graph that shows declines in a survival rate of yeasts due to the expression of the ordinary-temperature restriction enzyme that contains a yeast-derived intron.

As shown in FIG. 12, when compared with the control yeast, which carried a vector into which gene insertion had not been carried out, the ordinary-temperature restriction enzyme-expressing strains exhibited a reduction in the survival rate due to heating. In addition, this decline in the survival rate was observed regardless of the presence/absence of gene induction. It was suggested that, through the expression of the ordinary-temperature restriction enzyme MseI, DNA breakage was produced and exercised an effect on yeast growth.

A gene fragment for MseI protein expression was introduced into the prtTA-pADH1(Sc)-pCYC1-kanMX vector, which supports the induction of expression by doxycycline. The constructed plasmid vector was designated prtTA-pADH1(Sc)-pCYC1-iMseI(RUB1)-kanMX. prtTA-pADH1(Sc)-pCYC1-iMseI(RUB1)-kanMX and prtTA-pADH1(Sc)-pCYC1-kanMX as control were introduced into strain YPH499 of (S288C) lineage to obtain 3 strains of YPH499/prtTA-pADH1(Sc)-pCYC1-iMseI(RUB1)-kanMX and 1 strain of YPH499/prtTA-pADH1(Sc)-pCYC1-kanMX. All of the transformants were cultured for 24 hours at 25 deg C. on SD/MSG+G418 medium.

Gene expression was induced by the addition of 10 uM doxycycline and culture for 6 hours at 25 deg C. After the cells had been harvested by centrifugation, a cell extract was prepared by boiling and grinding with glass beads. The cell extract was adsorbed onto a membrane by western blotting. The FLAG protein was detected using anti-FLAG antibody and HRP-fused anti-mouse antibody. The results are given in FIG. 13.

Figure 13:
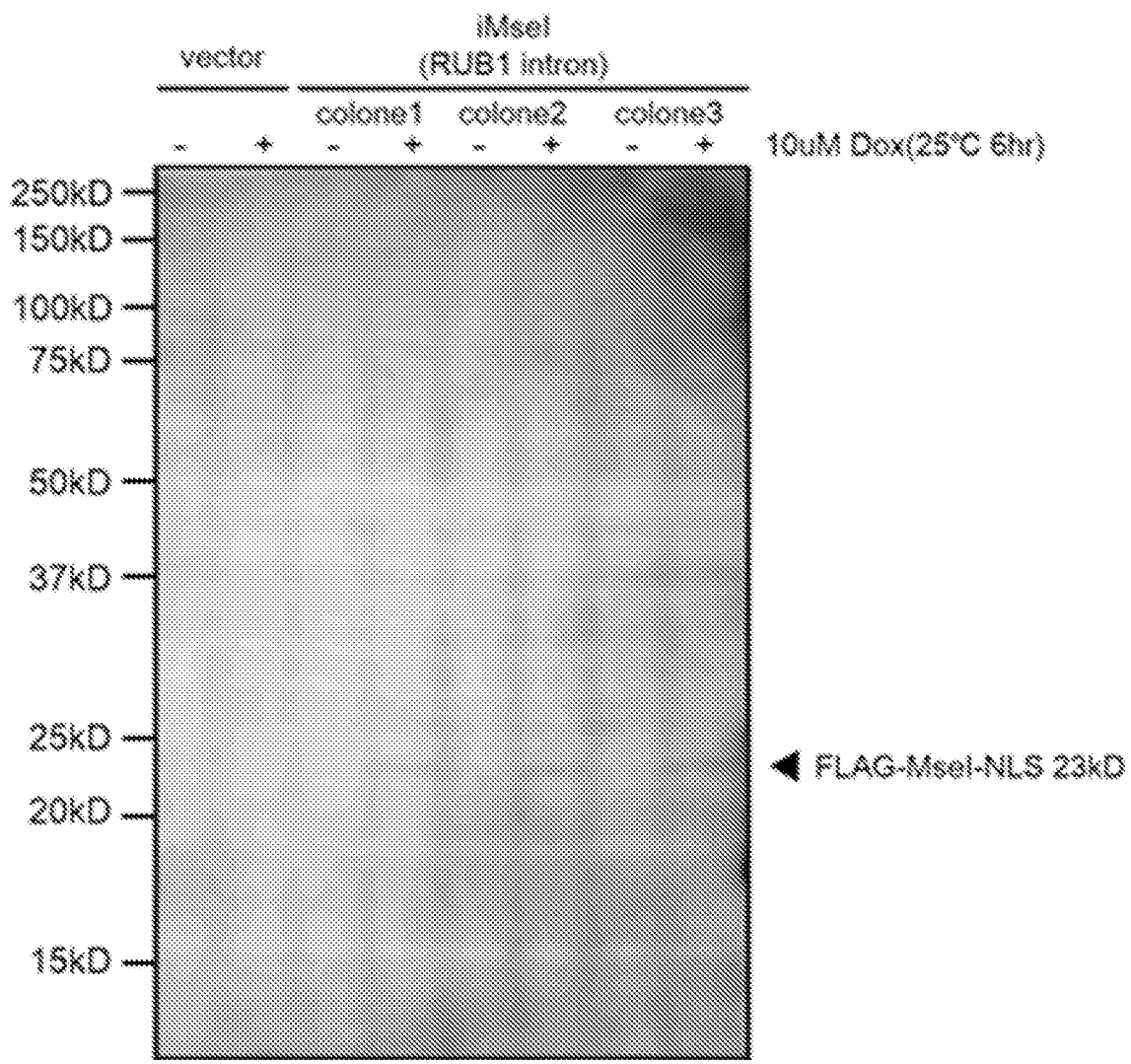
FIG. 13 is a photograph that shows an expression of the ordinary-temperature restriction enzyme in a protein level.

As shown in FIG. 13, a band between the 20 kilodalton and 25 kilodalton molecular weight markers was detected in the strain carrying prtTA-pADH1(Sc)-pCYC1-iMseI(RUB1)-kanMX. The predicted molecular weight for FLAG-iMseI-NLS is 23 kilodalton, and it is thought that the yeast intron has been excised and the ordinary-temperature restriction enzyme MseI has been expressed. Based on the preceding, it was suggested that, through the excision of the yeast intron and the expression of the ordinary-temperature restriction enzyme MseI, DNA breakage was produced and exercised an effect on yeast growth. Similarly, this suggested that genetic recombination is produced by DNA breakage in yeast.

Example 14

(14) Direct Introduction of Ordinary-Temperature Restriction Enzyme into Yeast

The strain YPH499 (S288C lineage) was cultured for 24 hours at 30 deg C. on SD medium (2% glucose, 0.67% yeast nitrogen base w/o amino acid, 0.1% monosodium glutamic acid, 10 mg/L adenine, 50 mg/L L-arginine, 50 mg/L L-aspartic acid, 20 mg/L L-histidine, 50 mg/L L-isoleucine, 100 mg/L L-leucine, 50 mg/L L-lysine, 20 mg/L L-methionine, 50 mg/L L-phenylalanine, 100 mg/L L-threonine, 50 mg/L L-tryptophan, 50 mg/L tyrosine, 20 mg/L uracil, 140 mg/L valine). The cells were washed twice with PBS solution and were suspended in 800 uL PBS solution.

30 uL Xfect (trademark) Protein Transfection Reagent (Takara Bio Inc.) was mixed with 170 uL deionized water. 100 uL of this solution was mixed with 85 uL buffer solution and 15 uL of a solution of the ordinary-temperature restriction enzyme HaeIII (New England Biolabs). In addition, 100 uL of the Reagent/deionized water mixture was mixed with 100 uL of the restriction enzyme solution-free buffer solution as control. These mixtures were held for 30 minutes at 25 deg C.

The cell suspension was equally divided and one portion was mixed with the HaeIII-free solution. The remaining cell suspension was mixed with the solution in which HaeIII was present. Both samples were cultured at quiescence for 2 hours at 30 deg C. After culture, both samples were washed twice with PBS and suspended in 500 uL PBS. Each sample was divided into fourths and these were heated, respectively, at 37 deg C. for 120 minutes, 60 minutes, or 30 minutes or at 25 deg C. for 120 minutes. The cells were diluted and plated to YPD plates and were cultured for 2 days at 30 deg C. and the survival rate was then measured. The results are given in FIG. 14.

Figure 14:
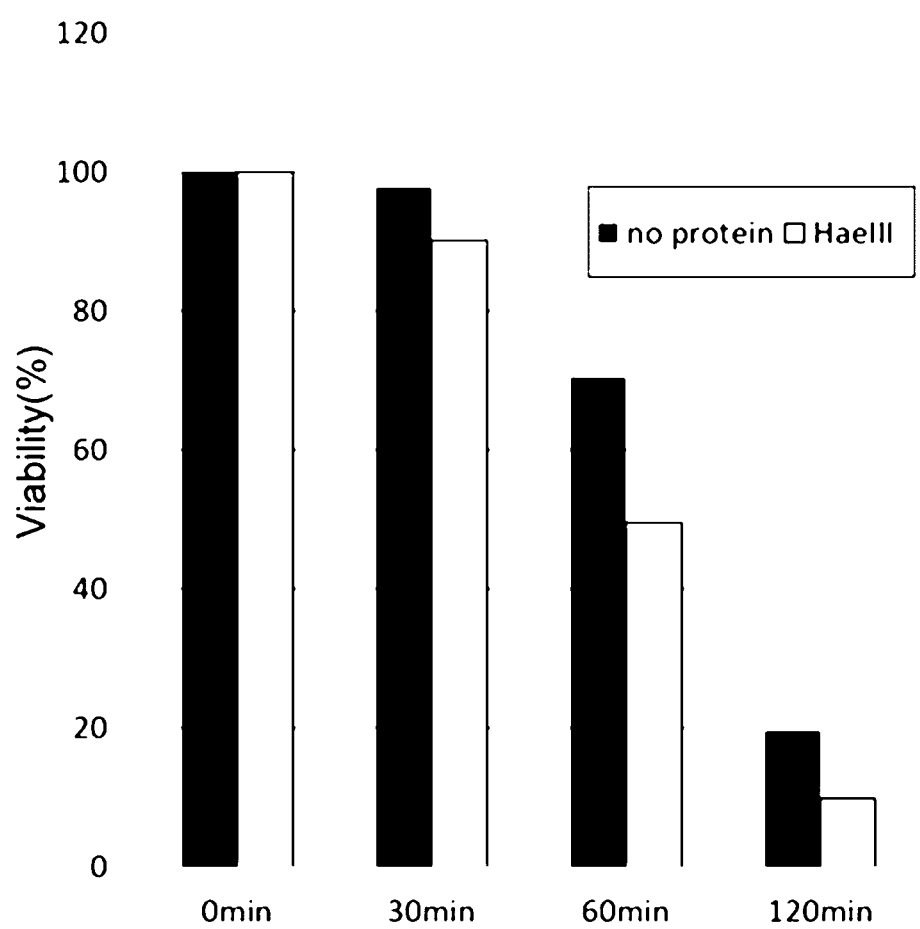
FIG. 14 is a diagram that shows declines in yeast survival rate due to direct introduction of the ordinary-temperature restriction enzyme protein.

As shown in FIG. 14, for heating at 37 deg C. for 30 minutes, 60 minutes, and 120 minutes, the cells mixed with the HaeIII-containing solution were shown to have a lower viability than the cells mixed with the control solution. Based on the preceding, it was suggested that, in yeast, the ordinary-temperature restriction enzyme HaeIII was incorporated into the cells and DNA breakage was produced and exercised an effect on yeast growth. Similarly, it was suggested that genetic recombination is produced by DNA breakage in yeast.

SEQUENCE TABLE FREE TEXT

SEQ ID NOS: 1 to 14: primers

The invention claimed is:

1. A method of modifying a genome of an organism, wherein the modification method comprises:
   modifying the genome of the organism by using, in a cell of the organism, a restriction enzyme having an optimal temperature for double-stranded DNA breakage activity in an ordinary temperature region,
   wherein:
   the restriction enzyme is obtained by expression of an exogenous gene that encodes the restriction enzyme,
   the exogenous gene has a coding region that contains an intron that is processed within the organism, but not processed within a host carrying this exogenous gene,
   the modification comprises double-stranded DNA breakages of endogenous DNA sequences that correspond to a recognition site of the restriction enzyme, and repairing at least a portion of the double-stranded DNA breakages with an endogenous DNA repair system, thereby modifying the genome of the organism,
   the restriction enzyme is selected from the group consisting of HinP1II, MseI, HaeIII, AluI, MboI, and HbaI, and
   the modifying is carried out at at least 20 deg C. and not more than 45 deg C.

2. The modification method according to claim 1, wherein the organism is a eukaryotic organism.

3. The modification method according to claim 1, wherein the modifying is carried out for at least 10 minutes and not more than 3 hours.

4. The modification method according to claim 1, wherein the modifying comprises controlling production of the restriction enzyme to a degree that enables modification of the genome while maintaining growth capacity of the organism.

5. The modification method according to claim 1, wherein the modifying comprises modifying the genome of the organism by inducing the expression of the exogenous gene.

6. The modification method according to claim 1, wherein the modifying comprises modifying the genome of the organism by continuous maintenance of the expression of the exogenous gene.

7. The modification method according to claim 1, wherein the organism is a plant body or a portion of a plant body.

8. The modification method according to claim 7, wherein the plant body or the portion of the plant body is one or more selected the group consisting of a seed, a shoot apex, a lateral bud, a flower bud, pollen, an ovary, an endosperm, and an embryo, and a portion of a seed, a shoot apex, a lateral bud, a flower bud, pollen, an ovary, an endosperm, and an embryo.

9. The modification method according to claim 1, wherein the organism is a microorganism.

10. A method of producing a population of genomically modified organisms, wherein the production method comprises:
    modifying a genome of a parent organism by causing an enzymatic activity, within a cell of the parent organism, of a restriction enzyme having an optimal temperature for double-stranded DNA breakage activity in an ordinary temperature region,
    wherein:
    the restriction enzyme is obtained by expression of an exogenous gene that encodes the restriction enzyme,
    the exogenous gene has a coding region that contains an intron that is processed within the parent organism, but not processed within a host carrying this exogenous gene,
    the modification comprises double-stranded DNA breakages of endogenous DNA sequences that correspond to a recognition site of the restriction enzyme, and repairing at least a portion of the double-stranded DNA breakages with an endogenous DNA repair system, thereby modifying the genome of the organism, the restriction enzyme is selected from the group consisting of HinP1I, MseI, HaeIII, AluI, MboI, and HbaI, and
    the modifying is carried out at at least 20 deg C. and not more than 45 deg C.

11. A method of producing a genomically modified organism, wherein the production method comprises:
    modifying a genome of a parent organism by causing an enzymatic activity, in a cell of the parent organism, of a restriction enzyme having an optimal temperature for double-stranded DNA breakage activity in an ordinary temperature region; and
    selecting an intended eukaryotic organism from a population of eukaryotic organisms that carry modified genomes based on an indicator, wherein:
the restriction enzyme is obtained by expression of an exogenous gene that encodes the restriction enzyme,
the exogenous gene has a coding region that contains an intron that is processed within the parent organism, but not processed within a host carrying this exogenous gene,
the modification comprises double-stranded DNA breakages of endogenous DNA sequences that correspond to a recognition site of the restriction enzyme, and repairing at least a portion of the double-stranded DNA breakages with an endogenous DNA repair system, thereby modifying the genome of the organism,
the restriction enzyme is selected from the group consisting of HinP1I, MseI, HaeIII, AluI, MboI, and HbaI, and
the modifying is carried out at at least 20 deg C. and not more than 45 deg C.

12. A breeding material comprising DNA that has a coding region that encodes a protein that has a double-stranded DNA breakage activity that exhibits an optimal temperature in an ordinary temperature region,
wherein:
the protein is selected from the group consisting of HinP1I, MseI, HaeIII, AluI, MboI, and HbaI, and
the coding region contains an intron that is not processed within a host for the breeding material.

13. The breeding material according to claim 12, which is an expression vector for a eukaryotic organism.

14. The breeding material according to claim 12, wherein the host is a prokaryotic organism.

15. The breeding material according to claim 13, wherein the eukaryotic organism is *Arabidopsis thaliana*.

16. The breeding material according to claim 14, wherein the host is *Agrobacterium*.

17. The breeding material according to claim 12, wherein the DNA includes an inducible promoter.

18. The breeding method according to claim 1, wherein the modifying is carried out at at least 30 deg C. and not more than 45 deg C.

19. The breeding method according to claim 1, wherein the modifying is carried out at at least 37 deg C. and not more than 45 deg C.

20. The breeding method according to claim 18, wherein the modifying is carried out for at least 10 minutes and not more than 3 hours.

* * * * *

UNITED STATES PATENT AND TRADEMARK OFFICE
CERTIFICATE OF CORRECTION

| | |
|---|---|
| PATENT NO. | : 11,248,232 B2 |
| APPLICATION NO. | : 16/060897 |
| DATED | : February 15, 2022 |
| INVENTOR(S) | : Hidenori Tanaka et al. |

It is certified that error appears in the above-identified patent and that said Letters Patent is hereby corrected as shown below:

In the Claims

Cancel the text of Claim 1 beginning with "1. A method of modifying a genome of an organism" and ending with "and not more than 45 deg C." and insert the following claim:
--1. A method of modifying a genome of an organism, wherein the modification method comprises:
 modifying the genome of the organism by using, in a cell of the organism, a restriction enzyme having an optimal temperature for double-stranded DNA breakage activity in an ordinary temperature region,
  wherein:
  the restriction enzyme is obtained by an expression of an exogenous gene that encodes the restriction enzyme,
  the exogenous gene has a coding region that contains an intron that is processed within the organism, but not processed within a host carrying this exogenous gene,
  the modification comprises double-stranded DNA breakages of endogenous DNA sequences that correspond to a recognition site of the restriction enzyme, and repairing at least a portion of the double-stranded DNA breakages with an endogenous DNA repair system, thereby modifying the genome of the organism,
  the restriction enzyme is selected from the group consisting of HinP1I, MseI, HaeIII, AluI, MboI, and HbaI, and
  the modifying is carried out at at least 20 deg C. and not more than 45 deg C.--

Cancel the text of Claim 10 beginning with "10. A method of producing a population of genomically modified organisms" and ending with "and not more than 45 deg C." and insert the following claim:
--10. A method of producing a population of genomically modified organisms, wherein the production method comprises:

Signed and Sealed this
Thirty-first Day of May, 2022

*Katherine Kelly Vidal*

Katherine Kelly Vidal
*Director of the United States Patent and Trademark Office* modifying a genome of a parent organism by causing an enzymatic activity, within a cell of the parent organism, of a restriction enzyme having an optimal temperature for double-stranded DNA breakage activity in an ordinary temperature region,
  wherein:
    the restriction enzyme is obtained by expression of an exogenous gene that encodes the restriction enzyme,
    the exogenous gene has a coding region that contains an intron that is processed within the parent organism, but not processed within a host carrying this exogenous gene,
    the modification comprises double-stranded DNA breakages of endogenous DNA sequences that correspond to a recognition site of the restriction enzyme, and repairing at least a portion of the double-stranded DNA breakages with an endogenous DNA repair system, thereby modifying the genome of the organism,
    the restriction enzyme is selected from the group consisting of HinP1I, MseI, HaeIII, AluI, MboL, and HbaL, and
    the modifying is carried out at at least 20 deg C. and not more than 45 deg C.--

Cancel the text of Claim 11 beginning with "11. A method of producing a genomically modified organism" and ending with "and not more than 45 deg C." and insert the following claim:
--11. A method of producing a genomically modified organism, wherein the production method comprises:
  modifying a genome of a parent organism by causing an enzymatic activity, in a cell of the parent organism, of a restriction enzyme having an optimal temperature for double-stranded DNA breakage activity in an ordinary temperature region; and
    selecting an intended eukaryotic organism from a population of eukaryotic organisms that carry modified genomes based on an indicator,
  wherein:
    the restriction enzyme is obtained by expression of an exogenous gene that encodes the restriction enzyme,
    the exogenous gene has a coding region that contains an intron that is processed within the parent organism, but not processed within a host carrying this exogenous gene,
    the modification comprises double-stranded DNA breakages of endogenous DNA sequences that correspond to a recognition site of the restriction enzyme, and repairing at least a portion of the double-stranded DNA breakages with an endogenous DNA repair system, thereby modifying the genome of the organism,
    the restriction enzyme is selected from the group consisting of HinP1I, MseI, HaeIII, AluI, MboI, and HbaI, and
    the modifying is carried out at at least 20 deg C. and not more than 45 deg C.--